(12) United States Patent
Vandersleen et al.

(10) Patent No.: US 9,885,706 B2
(45) Date of Patent: *Feb. 6, 2018

(54) PORTABLE CLINICAL ANALYSIS SYSTEM FOR IMMUNOMETRIC MEASUREMENT

(71) Applicant: Abbott Point of Care Inc., Princeton, NJ (US)

(72) Inventors: Gary Vandersleen, Plainsboro, NJ (US); Pierre Emeric, Princeton, NJ (US); Paul Wasserman, Oakhurst, NJ (US); Narendra Soman, Hillsborough, NJ (US); Graham Davis, Princeton, NJ (US); Cary Miller, Ottawa (CA)

(73) Assignee: Abbott Point of Care Inc., Princeton, NJ (US)

(*) Notice: Subject to any disclaimer, the term of this patent is extended or adjusted under 35 U.S.C. 154(b) by 310 days.

This patent is subject to a terminal disclaimer.

(21) Appl. No.: 14/099,398

(22) Filed: Dec. 6, 2013

(65) Prior Publication Data

US 2014/0170672 A1 Jun. 19, 2014

Related U.S. Application Data

(60) Provisional application No. 61/738,075, filed on Dec. 17, 2012.

(51) Int. Cl.
*G01N 21/00* (2006.01)
*G01N 33/53* (2006.01)
*G01N 33/49* (2006.01)

(52) U.S. Cl.
CPC ......... *G01N 33/5306* (2013.01); *G01N 33/49* (2013.01)

(58) Field of Classification Search
None
See application file for complete search history.

(56) References Cited

U.S. PATENT DOCUMENTS

| 5,096,669 A | 3/1992 | Lauks et al. |
| 5,600,576 A | 2/1997 | Broadwater et al. |
| 6,434,408 B1 | 8/2002 | Heckel et al. |
| 6,571,193 B1 | 5/2003 | Unuma et al. |
| 7,263,501 B2 | 8/2007 | Tirinato et al. |

(Continued)

FOREIGN PATENT DOCUMENTS

| CN | 1812744 | 8/2006 |
| CN | 101379386 | 3/2009 |

(Continued)

OTHER PUBLICATIONS

International Search Report and Written Opinion for PCT/US2013/073640 dated Mar. 7, 2014.

(Continued)

*Primary Examiner* — Chris L Chin
(74) *Attorney, Agent, or Firm* — Kilpatrick Townsend & Stockton LLP

(57) ABSTRACT

The present invention covers the integration and utility of accelerometer features into a clinical analysis system. For example, measurement of dynamic acceleration and orientation of a blood-testing instrument with respect to Earth's gravitational field may be used to determine reliability of a test procedure and optionally to provide corrective elements thereof.

19 Claims, 17 Drawing Sheets

(56) References Cited

U.S. PATENT DOCUMENTS

| | | | |
|---|---|---|---|
| 7,346,545 | B2 | 3/2008 | Jones |
| 7,419,821 | B2 | 9/2008 | Davis et al. |
| 8,158,062 | B2 | 4/2012 | Dykes et al. |
| 9,377,475 | B2* | 6/2016 | Emeric ............... B01L 3/50273 |
| 2005/0235385 | A1 | 10/2005 | Wehrenberg et al. |
| 2007/0166195 | A1 | 7/2007 | Padmanabhan et al. |
| 2008/0025872 | A1 | 1/2008 | Dykes et al. |
| 2008/0297169 | A1 | 12/2008 | Greenquist et al. |
| 2009/0312615 | A1 | 12/2009 | Caduff et al. |
| 2011/0150705 | A1 | 6/2011 | Doyle et al. |
| 2011/0151491 | A1 | 6/2011 | Dennis et al. |
| 2011/0257496 | A1 | 10/2011 | Terashima et al. |
| 2012/0081812 | A1 | 4/2012 | Lin et al. |
| 2013/0162981 | A1* | 6/2013 | Emeric .................. G01N 33/48 356/72 |
| 2013/0230913 | A1 | 9/2013 | Florescu |
| 2013/0300559 | A1 | 11/2013 | Chien et al. |
| 2013/0334041 | A1 | 12/2013 | Kondo et al. |
| 2013/0343955 | A1 | 12/2013 | Doyle et al. |
| 2014/0046160 | A1 | 2/2014 | Terashima et al. |
| 2014/0170694 | A1* | 6/2014 | Vandersleen ...... G01N 33/5091 435/29 |
| 2014/0172315 | A1* | 6/2014 | Vandersleen .... G01N 33/48785 702/19 |
| 2014/0172316 | A1* | 6/2014 | Vandersleen .......... G01N 33/49 702/19 |
| 2014/0172341 | A1* | 6/2014 | Vandersleen ...... G01N 27/3273 702/89 |
| 2017/0030888 | A1 | 2/2017 | Vandersleen et al. |

FOREIGN PATENT DOCUMENTS

| | | |
|---|---|---|
| CN | 102116743 | 7/2011 |
| CN | 104956212 | 9/2015 |
| CN | 104956222 | 9/2015 |
| CN | 105008920 | 10/2015 |
| WO | 2012132432 | 10/2012 |
| WO | 2013096804 | 6/2013 |
| WO | 2014/099471 | 6/2014 |

OTHER PUBLICATIONS

U.S. Appl. No. 61/579,816, filed Dec. 23, 2011, Emeric, et al.
FDA publication, "Recommendations Clinical Laboratory Improvement Amendments of 1998 (CLIA) waiver applications for Manufacturers of In Vitro Diagnostics Devices", Jan. 30, 2008.
"International Search Report and Written Opinion for PCT/US2013/073633", dated Mar. 6, 2014, 9 Pages.
"Non-Final Office Action" for U.S. Appl. No. 14/099,419, dated Oct. 7, 2016, 13 pages.
"Final Office Action" for U.S. Appl. No. 14/099,470, dated Apr. 13, 2016, 12 pages.
"Non-Final Office Action" for U.S. Appl. No. 14/099,470, dated Feb. 26, 2015, 10 pages.
"Notice of Allowance" for U.S. Appl. No. 14/099,470, dated Aug. 25, 2016, 7 pages.
"Final Office Action" for U.S. Appl. No. 14/099,479, dated Aug. 17, 2016, 20 pages.
"Non-Final Office Action" for U.S. Appl. No. 14/099,479, dated Mar. 3, 2016, 15 pages.
"Non-Final Office Action" for U.S. Appl. No. 14/099,504, dated Oct. 7, 2016, 16 pages.
"Office Action" for CN201380071676.3, dated Jun. 27, 2016, 17 pages.
"Office Action" for CN201380071670.6, dated Oct. 18, 2016, 17 pages.
"International Preliminary Report on Patentability" for PCT/US2013/073633, dated Jul. 2, 2015, 7 pages.
"International Preliminary Report on Patentability" for PCT/US2013/073637, dated Jul. 2, 2015, 12 pages.
"International Preliminary Report on Patentability" for PCT/US2013/073639, dated Jul. 2, 2015, 7 pages.
"International Preliminary Report on Patentability" for PCT/US2013/073642, dated Jul. 2, 2015, 12 pages.
"International Search Report and Written Opinion" for PCT/US2013/073642, dated May 13, 2014, 14 pages.
"Advisory Action", issued in U.S. Appl. No. 14/099,419, dated Jun. 16, 2017, 7 pages.
"Final Office Action", issued in U.S. Appl. No. 14/099,419, dated Mar. 23, 2017, 12 pages.
"First Action Interview Office Action Summary", issued in U.S. Appl. No. 14/099,479, dated Jun. 6, 2017, 4 pages.
"Non-Final Office Action", issued in U.S. Appl. No. 15/291,454, dated Jun. 1, 2017, 10 pages.
"Non-Final Office Action" issued U.S. Appl. No. 14/099,419, dated Aug. 11, 2017, 19 pages.
"Final Office Action" issued U.S. Appl. No. 14/099,504, dated Jul. 14, 2017, 23 pages.
"Notice of Allowance" issued in U.S. Appl. No. 14/099,504, dated Nov. 30, 2017, 13 pages.
"Notice of Allowance" issued in U.S. Appl. No. 15/291,454, dated Nov. 6, 2017, 7 pages.
Notice of Allowance issued in U.S. Appl. No. 14/099,419, dated Dec. 22, 2017, 16 pages.

* cited by examiner

PORTABLE CLINICAL ANALYSIS SYSTEM FOR IMMUNOMETRIC MEASUREMENT

CROSS REFERENCE TO RELATED APPLICATIONS

This application claims priority to U.S. Provisional Application No. 61/738,075 filed on Dec. 17, 2012, the entirety of which is hereby incorporated by reference.

FIELD OF THE INVENTION

The invention relates to analytical testing devices. Specifically, the invention relates to devices, systems and methods for using acceleration and orientation/inclination data in point-of-care analyte testing systems.

BACKGROUND OF THE INVENTION

Traditionally, testing of blood or other body fluids for medical evaluation and diagnosis was the exclusive domain of large, well-equipped central laboratories. While such laboratories offer efficient, reliable, and accurate testing of a high volume of fluid samples, they cannot offer rapid turn-around of results to enable more immediate medical decision making. A medical practitioner typically must collect samples, transport them to a laboratory, wait for the samples to be processed and then wait for the results to be communicated. Even in hospital settings, the handling of a sample from the patient's bedside to the hospital laboratory produces significant delays. This problem is compounded by the variable workload and throughput capacity of the laboratory and the compiling and communicating of data.

The introduction of point-of-care analyte testing systems enabled practitioners to obtain immediate test results while examining a patient, whether in the physician's office, the hospital emergency room, or at the patient's bedside. To be effective, a point-of-care analyte device must provide error-free operation for a wide variety of tests in relatively untrained hands. For optimum effectiveness, a real-time system requires minimum skill to operate, while offering maximum speed for testing, appropriate accuracy and system reliability, as well as cost effective operation. A notable point-of-care system (The i-STAT® System, Abbott Point of Care Inc., Princeton, N.J.) is disclosed in U.S. Pat. No. 5,096,669, which comprises a disposable device, operating in conjunction with a hand-held analyzer, for performing a variety of measurements on blood or other fluids.

However, unique obstacles and challenges have arisen with the advent of point-of-care analyte testing systems that may impede error-free operation of these systems in relatively untrained hands. Specifically, in the traditional central laboratories, the analyte testing systems are large and placed in fixed locations within the laboratory such that the instrumentation is rarely influenced by the effects of motion or device impact. However, with point-of-care analyte testing systems, the instrumentation is generally small and portable, e.g., a handheld mobile device, such that the probability of the instrumentation being influenced from the effects of motion and device impacts is significantly greater. For example, it is not uncommon for point-of-care analyte testing systems to be dropped or jostled by relatively untrained hands prior to or during operation. The dropping or jostling of point-of-care analyte testing systems prior to or during operation may have disadvantageous effects on the operation of the systems. Accordingly, there exists a need in the art to improve upon the overall quality of point-of-care analyte testing systems by ameliorating the effect of motion or device impact on the point-of-care analyte testing systems.

SUMMARY OF THE INVENTION

In one embodiment, the present invention is directed to a portable clinical system for performing an immunoassay, the system including a test device comprising an immunosensor and an analyzer including a port configured to receive the test device and a computing device configured to determine motion of the analyzer during a test cycle of the test device. The computing device is further configured to compare the determined motion to a threshold rate of motion for the test device, and at least one of providing an alert prompting a user to take corrective action during the test cycle, correcting a result of the immunoassay, and/or suppressing the result of the immunoassay, when the determined motion exceeds the threshold rate of motion.

In addition, the computing device may be further configured to determine spatial orientation of the analyzer during the test cycle of the test device, compare the determined spatial orientation to a threshold operating spatial plane for the test device, and at least one of providing a different alert prompting the user to take different corrective action during the test cycle, correcting the result of the immunoassay, and/or suppressing the result of the immunoassay, when the determined spatial orientation exceeds the threshold operating spatial plane.

In addition, the computing device is optionally configured to measure static acceleration on at least three axes of the analyzer to determine the spatial orientation of the analyzer, and the determining the spatial orientation comprises determining at least one of roll, pitch, and yaw of the analyzer based on the measured static acceleration on at least three axes of the analyzer.

In another embodiment, a method is provided performing an immunoassay, the method comprising inserting a test device comprising an immunosensor into a port of an analyzer, initiating a test cycle of the test device, determining motion of the analyzer during the test cycle of the test device, comparing the determined motion to a threshold rate of motion for the test device, and at least one of providing an alert prompting a user to take corrective action during the test cycle, correcting a result of the immunoassay, and/or suppressing the result of the immunoassay, when the determined motion exceeds the threshold rate of motion.

In addition, the method may further comprise determining motion of the analyzer during the test cycle of the test device, comparing the determined motion to a threshold rate of motion for the test device, and at least one of providing the alert prompting the user to take corrective action during the test cycle, and/or suppressing the result of the analytical test, when at least one of the determined spatial orientation exceeds the threshold operating spatial plane, and/or the determined motion exceeds the threshold rate of motion.

In addition, the method optionally comprises determining a stage of the test cycle and determining the threshold rate of motion based on the determined stage of the test cycle.

In another embodiment, a method is provided performing an immunoassay, the method comprising inserting a blood sample into a test device comprising a conduit with an immunosensor, initiating a test cycle of the test device, determining motion of an analyzer during the test cycle of the test device, comparing the determined motion to a threshold rate of motion for the test device, and at least one of providing an alert prompting a user to take corrective action during the test cycle, and/or correcting or suppressing a result of the immunoassay, when the determined motion exceeds the threshold rate of motion.

BRIEF DESCRIPTION OF THE DRAWINGS

The present invention will be better understood in view of the following non-limiting figures, in which.

DETAILED DESCRIPTION OF THE INVENTION

Introduction

Figure 1A:
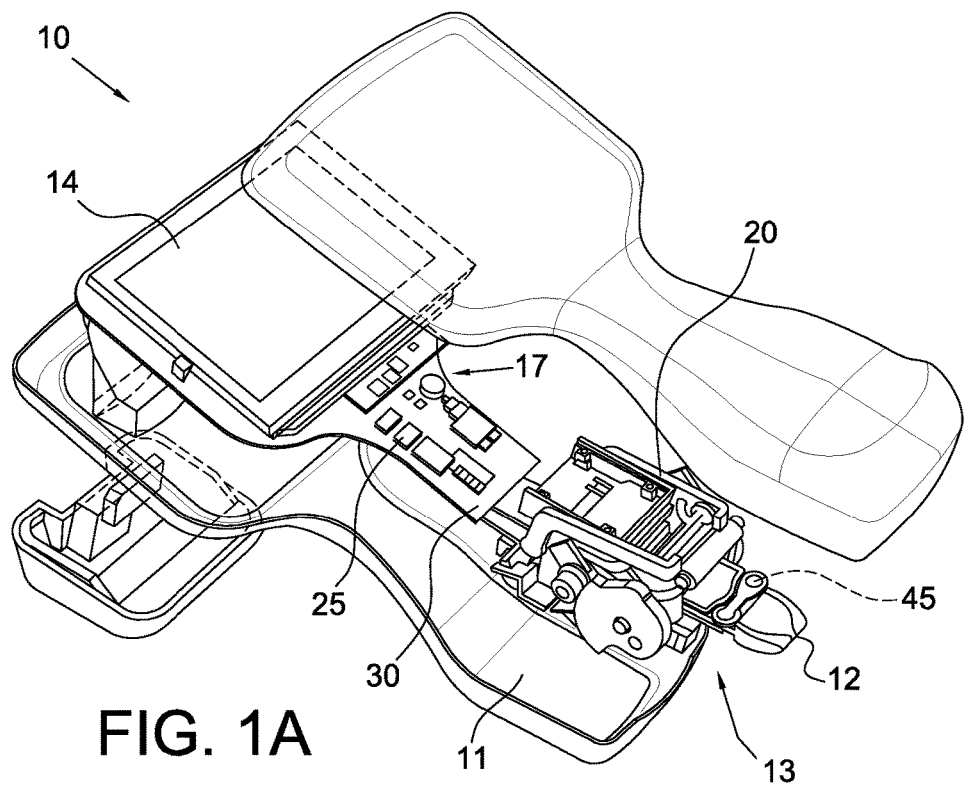
FIG. 1A shows an exploded view of an analyzer with a cartridge inserted therein in accordance with some aspects of the invention.

The present invention relates to a handheld In-Vitro Diagnostic (IVD) instrument system including a self-contained disposable sensing device or cartridge and a reader or analyzer configured for use at a patient bedside. A fluid sample to be measured is drawn into a sample entry orifice or port in the cartridge and the cartridge is inserted into the analyzer through a slotted opening or port. Measurements performed by the analyzer are output to a display or other output device, such as a printer or data management system via a port on the analyzer to a computer port. Transmission can be via Wifi, Bluetooth link, infrared and the like. For example, the handheld IVD instrument system may be of similar design to the systems disclosed in jointly owned U.S. Pat. No. 5,096,669 and U.S. Pat. No. 7,419,821, both of which are incorporated herein by reference in their entireties.

The analyzer is preferably designed as a mobile device such that it can be hand carried to the location of the patient, e.g., the patient's bedside, when a user needs to perform an analytical test, e.g., a blood test. As with any mobile device, occasional drops and bumps into solid surfaces occur during handling and transport. Mechanical abuse such as cracked bezel windows, enclosures, battery doors, internal damage to the electro-mechanical measurement module, etc., that result from device mishandling may disadvantageously influence analytical results. Although forensic investigations (when analyzers are returned to the factory) reveal that mechanical abuse of analyzers is common, no precise data exists to characterize typical operating environments of the analyzers that may provide insight into the circumstances surrounding the mechanical abuse. Accordingly, the invention, in some embodiments, provides a system for determining and recording the operating environment of an analyzer.

An additional difficulty associated with performing analyte testing on a handheld or mobile platform involves a requirement for stability or lack of motion when the analyzer is performing fluidics actuation and electro-chemical or optical measurements. During parts of the testing cycle, precise motion actuation of the sample in the cartridge is required. Inertial forces due to the analyzer being moved by the operator may create uncontrolled and disadvantageous fluid motion. However, this effect does not apply to all tests to the same extent. While some test procedures may exhibit this sensitivity, other test procedures may be less susceptible to error resulting from inertial forces. Tests that are less susceptible to such error generally include those that are not affected by the settling of blood cells within a sample, or not affected by fluid motion or mixing. Accordingly, further implementations of the invention provide a system for identifying circumstances during which analyte testing is subjected to inertial forces and providing counter measures to offset or eliminate the effect of the inertial forces and/or correct for the occurrence of the inertial forces.

Another difficulty that may be associated with performing analyte testing on a handheld or mobile platform involves requirements for spatial orientation of the analyzer during the measurement cycle of some analytical tests. The spatial orientation of the analyzer can be described as motion about three axes of the analyzer, defined as roll, pitch, and yaw. As cells in whole blood can at least partially sediment, e.g., on a sensor of a cartridge placed in the analyzer, and interfere with fluid flow, it may be important in some instances to properly orient the analyzer and test cartridge with respect to Earth's gravitational field. For example, a rate of cell sedimentation with respect to the analyzer may be dependent on the spatial orientation and/or the motion of the reader during a test cycle. Some assays, such as hematocrit, activated clotting time (ACT), prothrombin time international normalized ratio (PT INR), and cardiac markers (e.g., troponin I (cTnI), B-type natriuretic peptide (BNP), and creatine kinase myocardial band (CKMB)), are more sensitive than others to this effect.

Without instrumented measurement of the dynamic acceleration and the orientation of the analyzer, the operator may be relied upon to ensure that the analyzer is stable and properly positioned on a horizontal surface for substantially the entire duration of the measurement cycle. The time period required for completing analytical tests may range, for example, from approximately 2 to 20 minutes. In a busy hospital environment, it may be desirable to free up the healthcare staff from attending to the analyzer while the test is running and allow the staff to receive feedback if the analyzer is either unstable, improperly positioned, or has been moved during the test cycle. Accordingly, further implementations of the invention provide a system for identifying circumstances during which the analyte testing is subjected to inertial forces and providing notification of the detection of the inertial forces, counter measurements to offset or eliminate the effect of the inertial forces, and/or correct for the occurrence of the inertial forces. More specifically, one embodiment of the present invention uses inertial data collected by on-board accelerometers to detect, and react to, disadvantageous motion of the analyzer during critical measurement cycle phases; provide positioning information to the user with respect to Earth's gravity; and provide other functionalities made possible by the knowledge of inertial information.

IVD Instrument System

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more non-transitory computer readable storage medium(s) having computer readable program code embodied thereon.

Figure 1B:
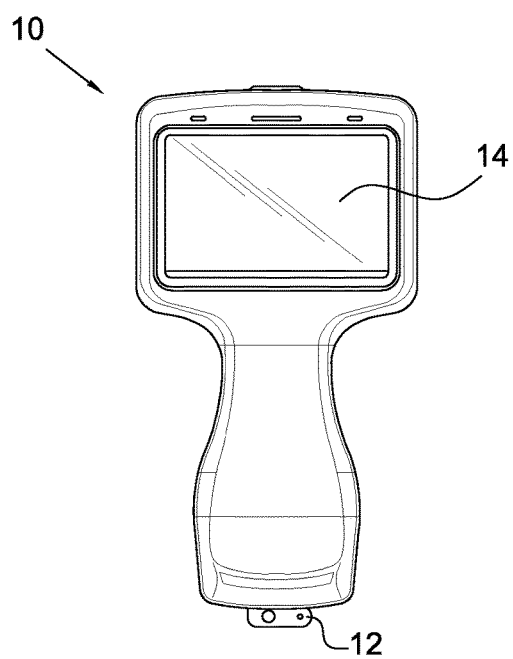
FIG. 1B shows a top view of an analyzer with a cartridge inserted therein in accordance with some aspects of the invention.
Figure 1C:
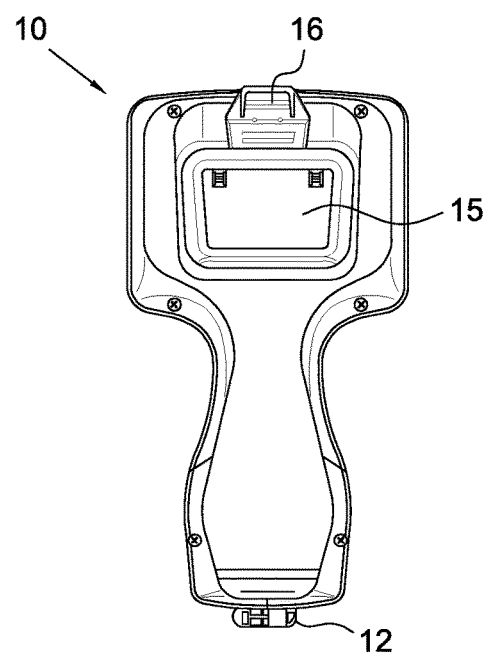
FIG. 1C shows a bottom view of an analyzer with a cartridge inserted therein in accordance with some aspects of the invention.

FIGS. 1A-1C depict an analyzer 10 with a base 11 and a cartridge 12 (e.g., a test device) inserted within a universal port 13 of the analyzer 10, e.g., an i-STAT™ handheld analyzer with an i-STAT™ cartridge inserted therein, as described in jointly owned U.S. Pat. No. 5,096,669 and U.S. Pat. No. 7,419,821. The cartridge 12 includes a sample entry port 45 that is substantially aligned to a plane parallel to a horizontal plane of the base 11. The analyzer 10 includes a display 14, a battery pack 15, and a reader 16, e.g., a 2D barcode scanner. The analyzer 10 further includes a computing device 17 that interfaces with various cartridges 12 via the port 13.

The computing device 17 can be resident on a network infrastructure, e.g., a hospital intranet. The computing device 17 also preferably includes a processor, memory, an I/O interface, and a bus. The bus provides a communications link between each of the components in the computing device 17. The memory can include local memory employed during actual execution of program code, bulk storage, and cache memories that provide temporary storage of at least some program code in order to reduce the number of times code must be retrieved from bulk storage during execution. In addition, the computing device 17 preferably includes random access memory (RAM), a read-only memory (ROM), and an operating system (O/S).

In general, the processor is configured to execute computer program code, which can be stored in the memory. While executing the computer program code, the processor can read and/or write data to/from memory. The program code executes the processes of the invention. For example, in accordance with some aspects of the invention, the program code controls a measurement module 20 and one or more accelerometers 25, which perform the processes described herein. In additional or alternative embodiments, the program code may also be configured to control one or more on-board sensors additional to that of the accelerometers 25, e.g., a temperature sensor, an ambient light sensor, a barometric pressure sensor, an imaging camera, etc, which may be used for various functions of the analyzer 10. The measurement module 20 can be implemented as one or more program code in the program control stored in the memory as separate or combined modules. Additionally, the measurement module 20 may be implemented as separate dedicated processors, a single processor, or several processors to provide the function of the module.

The measurement module 20 is configured to interact with the cartridge 12 in multiple ways. For example, the measurement module 20 may determine the type of cartridge 12 inserted into the analyzer 10 using for example the imaging camera to capture data from a bar code positioned on the cartridge, secure the cartridge 12 mechanically, establish electrical connections with sensors in the cartridge 12, regulate the temperature of the cartridge 12 during a test cycle using for example the temperature sensor, actuate calibration and sample fluids according to pre-established cycles, and optionally acquire images using for example the imaging camera of areas located on the cartridge 12, e.g., the underside of the cartridge.

To this extent, the functionality provided by the computing device 17 of the analyzer 10 can be implemented by a computing article of manufacture that includes any combination of general and/or specific purpose hardware and/or computer program code. In each embodiment, the program code and hardware can be created using standard programming and engineering techniques, respectively.

The accelerometer 25 is mounted on an electronic board 30 within the analyzer 10. The measurement module 20 and the electronic board 30 are both secured in the analyzer 10 with fasteners and aligned with reference surfaces. The measurement module 20 is configured to precisely and securely position the cartridge 12 in place when the cartridge 12 is interfaced with measurement module 20 through the port 13. Therefore, in accordance with some aspects of the invention the computing device is configured to determine the orientation and acceleration of the analyzer by itself or both the analyzer 10 and the cartridge 12 (when inserted into the measurement module 20) by means of the accelerometer 25.

The one or more accelerometers 25 are electromechanical devices that measure acceleration. Acceleration is the rate at which the velocity of a body changes over time. Proper acceleration is the physical acceleration experienced by an object. Accelerometers are devices that measure proper acceleration. Therefore, the acceleration measured by an accelerometer is not necessarily the rate of change of velocity. For example, an accelerometer at rest on the surface of the earth will measure an acceleration of g=9.81 m/s$^2$. Accelerometers in free fall will measure zero acceleration. The term "acceleration" as used herein indicates "proper acceleration" or acceleration measured by the accelerometer.

Acceleration forces may be static, like the constant force of gravity pulling objects towards the Earth's surface, or they may be dynamic, e.g., caused by moving or vibrating the accelerometer. By measuring the amount of static acceleration due to gravity, it is possible to determine the angle the device is tilted at with respect to Earth's gravitational field. By sensing the amount of dynamic acceleration, it is possible to analyze the direction or manner in which the device is moving. The operating principle of the accelerometer can be described as a simple mass supported on a damped spring. The mass is displaced when the accelerometer experiences acceleration. Measurement of the displacement of the mass is used to derive the acceleration. Piezoelectric, piezoresistive, and capacitive components are used in commercially available accelerometers to convert displacement into an electrical signal. Other forms of accelerometers may also be used.

Several accelerometers, e.g., ADXL345 (Analog Devices, Inc.), MMA7260Q (Freescale Semiconductor, Inc.), and H48C (Hitachi) are commercially available and may be implemented in the present invention. For example, the ADXL345 includes a small, thin, ultra-low power, 3-axis accelerometer with high resolution (13-bit) measurement at up to ±16 g. The ADXL345 may be well suited for mobile device applications. The ADXL345 measures the static acceleration of gravity in tilt-sensing applications, as well as dynamic acceleration resulting from motion or shock. The ADXL345's high resolution (3.9 mg/LSB) enables measurement of inclination changes less than 1.0°. Threshold values can be assigned for both dynamic acceleration and angle deviation from rest position. However, it should be understood that the present invention is not limited to these exemplary accelerometers.

Figure 2:
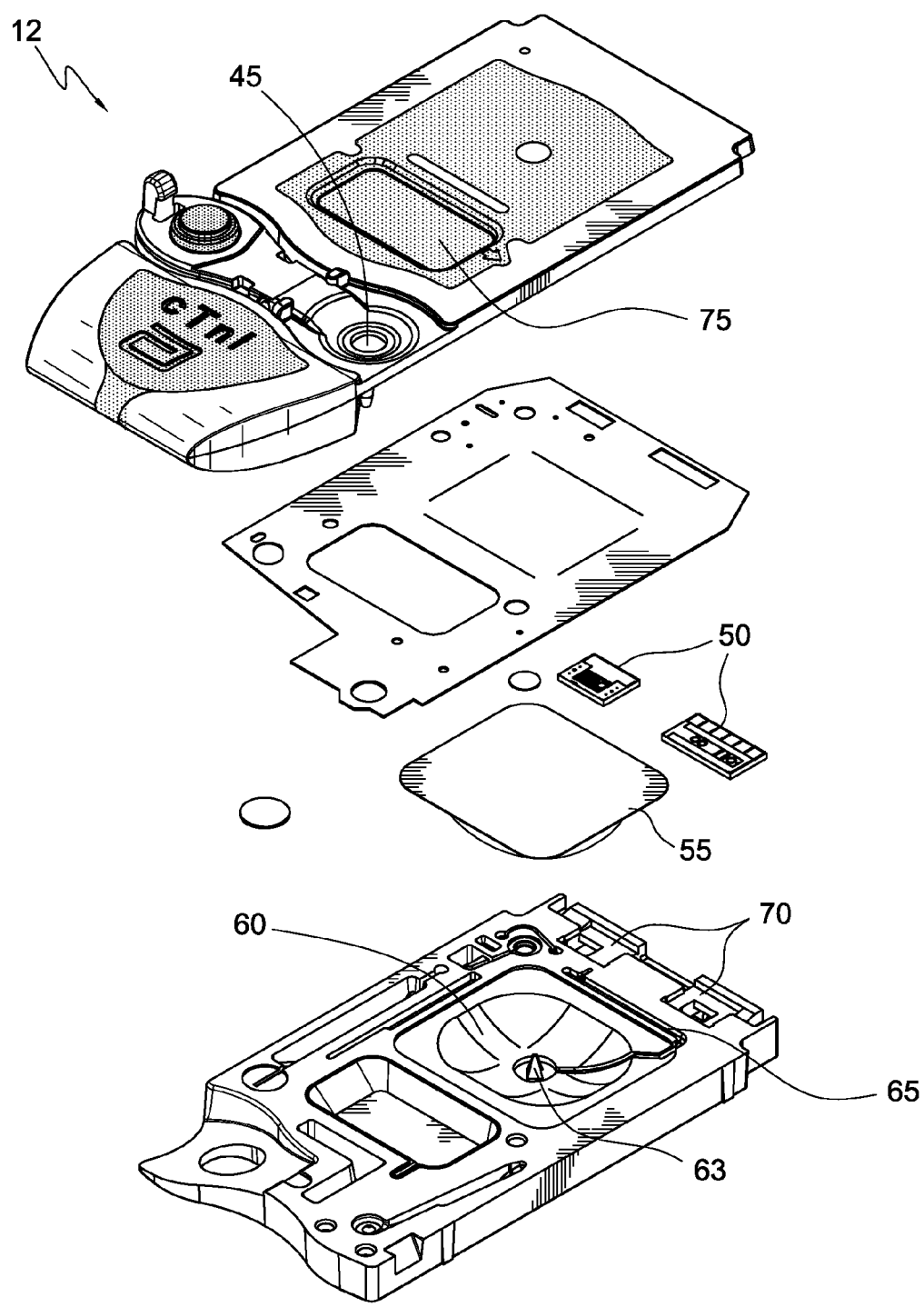
FIG. 2 shows an exploded view of a cartridge in accordance with some aspects of the invention.

FIG. 2 shows an exploded view of cartridge 12 as described in jointly owned U.S. Patent Application Publication No. 2011/0150705 and U.S. patent application Ser. No. 13/530,501. The cartridge 12 comprises a sample entry port 45, at least one sensor 50 (e.g., an electrochemical sensor, an immunosensor, a hematocrit sensor, a conductivity sensor, etc.), and a pouch 55 containing a fluid, e.g., a sensor-standardization, calibration fluid, and/or wash fluid. The at least one sensor 50 is substantially aligned to a plane parallel to a horizontal plane of the base of the analyzer. A recessed region 60 of the cartridge 12 preferably includes a spike 63 configured to rupture the pouch 55, upon application of a force upon the pouch 55, for example, by the analyzer 10 (shown in FIG. 1). Once the pouch 55 is ruptured, the system is configured to deliver the fluid contents from the pouch 55 into a conduit 65. Movement of the fluid into and through the conduit 65 and to a sensor region 70 (e.g., a conduit comprising the at least one sensor 50 and a sensing reagent for the sensor) may be effected by a pump, e.g., a pneumatic pump connected to the conduit 65. Preferably, the pneumatic pump comprises a displaceable membrane 75. In the embodiment shown in FIG. 2, the cartridge 12 or test device is configured to pump fluid via the displaceable membrane 75 from the ruptured pouch 55 and the sample entry port 45 through the conduit 65 and over the sensor region 70. The at least one sensor 50 generates electric signals based on a concentration of specific chemical species in the sample, e.g., performs an immunoassay on a blood sample from a patient.

The analytes/properties to which the at least one sensor responds generally may be selected from among hematocrit, troponin, CKMB, BNP, beta human chorionic gonadotropin (bHCG), carbon dioxide partial pressure ($pCO_2$), partial pressure oxygen ($pO_2$), pH, PT, ACT, activated partial thromboplastin time (APTT), sodium, potassium, chloride, calcium, urea, glucose, creatinine, lactate, oxygen, and carbon dioxide, thyroid stimulating hormone, parathyroid hormone, D-dimer, prostate specific antibody and the like, and combinations thereof. Preferably, the analyte is tested in a liquid sample that is whole blood, however other samples can be used including blood, serum, plasma, urine, cerebrospinal fluid, saliva and amended forms thereof. Amendments can include diluents and reagents such as anticoagulants and the like.

FIGS. 4, 6-10, 12-14, and 18 show exemplary flowcharts for performing the process steps of the present invention. The steps of FIGS. 4, 6-10, 12-14, and 18 may be implemented using the computing device described above with respect to FIGS. 1A-1C. Specifically, the flowcharts in FIGS. 4, 6-10, 12-14, and 18 illustrate the architecture, functionality, and operation of possible implementations of the systems, methods and computer program products according to several embodiments of the present invention. In this regard, each block in the flowcharts may represent a module, segment, or portion of code, which comprises one or more executable instructions for implementing the specified logical function(s). It should also be noted that, in some alternative implementations, the functions noted in the blocks may occur out of the order noted in the figure. For example, two blocks shown in succession may, in fact, be executed substantially concurrently, or the blocks may sometimes be executed in the reverse order, depending upon the functionality involved. It will also be noted that each block of the flowchart illustrations, and combinations of blocks in the flowchart illustrations, can be implemented by special purpose hardware-based systems that perform the specified functions or acts, or combinations of special purpose hardware and computer instructions.

Detection of Improper Orientation During Testing

In one embodiment of the present invention, the computing device is configured to measure static acceleration using the accelerometer and formulate a determination on whether one or more actions should be triggered based on the measured static acceleration. As discussed above, in some embodiments, the accelerometer is configured to measure inclination changes (e.g., inclination changes of less than about 1.0°) of the analyzer by itself or of both the analyzer and the cartridge during a test cycle after the cartridge has been inserted into the measurement module. Since some assays are sensitive to inclination changes (e.g., hematocrit, ACT, PT INR, and cardiac markers such as cTnI, BNP, and CKMB), it is important to keep the analyzer properly positioned on a flat horizontal surface for substantially the entire duration of a test cycle for these analytes.

Figure 3:
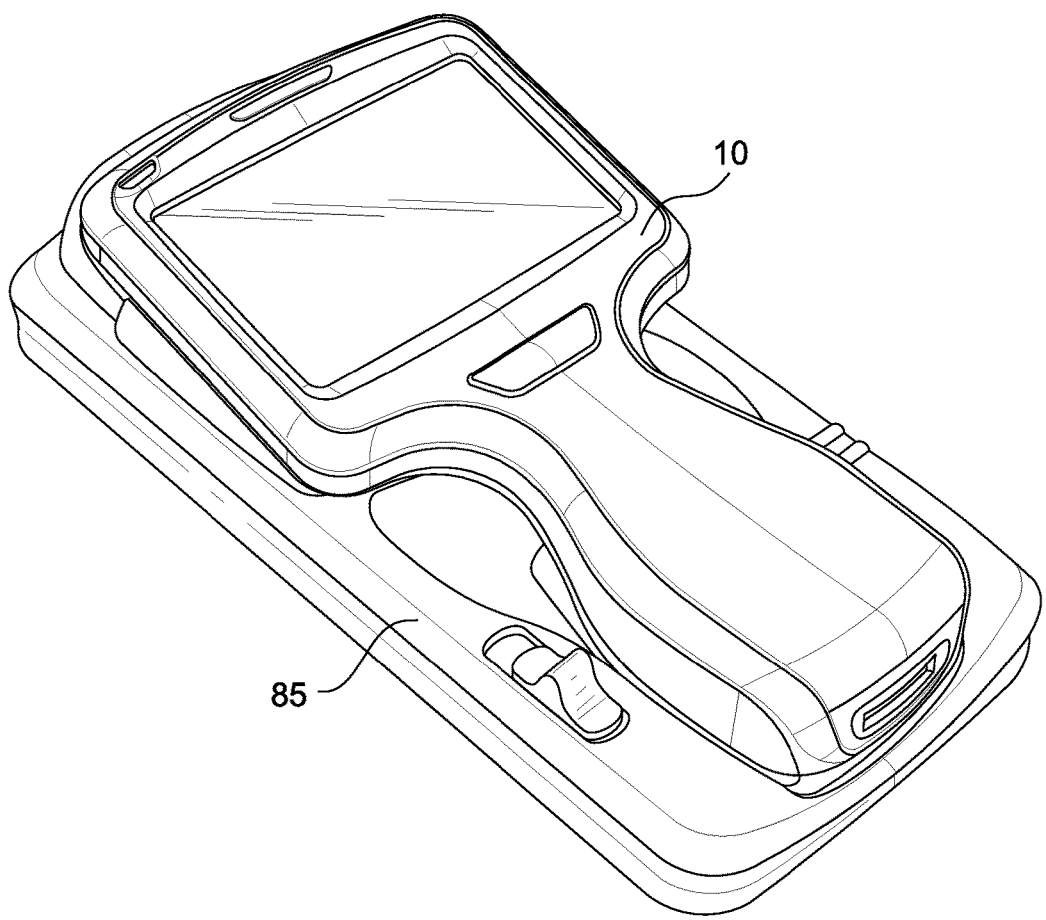
FIG. 3 shows a perspective view of a analyzer in a docking station in accordance with some aspects of the invention.

For example, when not in use, analyzer 10 may be docked in a downloader/recharge station (base station) 85, as shown in FIG. 3. The base station 85 may be configurable as a bench top (horizontal) or wall-mount (vertical) unit. In the wall-mount configuration, the analyzer is positioned vertically and therefore should not be used for testing unless the orientation of the reader is modified such that the cartridge is substantially horizontal while the reader is in the vertical position. The accelerometer can detect the angle of the analyzer and send the angle measurement information to the computing device. By comparing the angle of the analyzer to at least one predetermined threshold (e.g., a first threshold related to the bench top (horizontal) configuration of the docked analyzer 10 and/or a second threshold related to the wall-mount (vertical) configuration of the docked analyzer), the computing device can trigger one or more actions, e.g., authorize or disable testing and/or display a warning message to the operator. Accordingly, some aspects of the invention provide systems and processes for monitoring inclination changes of the analyzer during operation to ensure that the analyzer remains in a substantially horizontal position.

Figure 4:
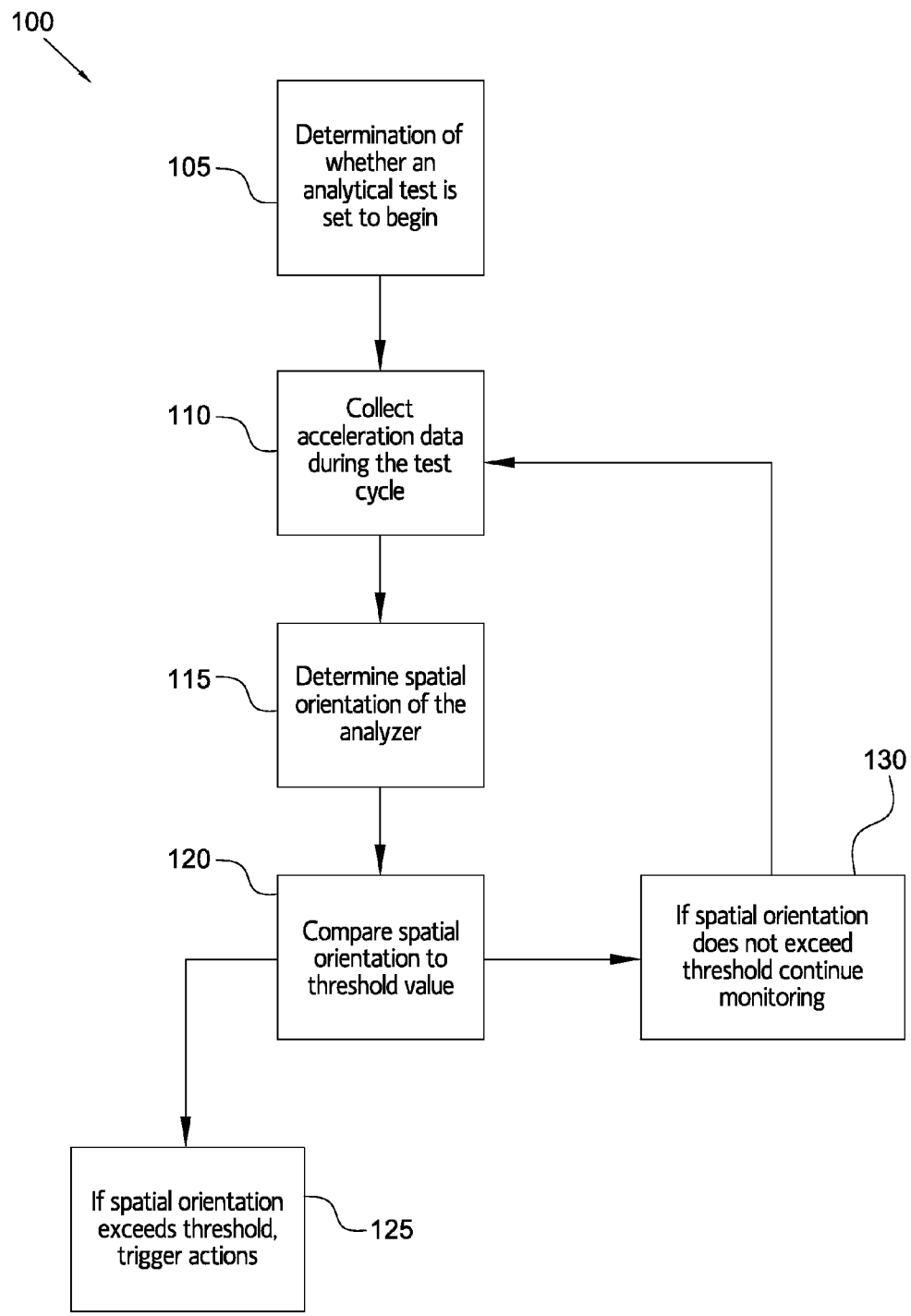
FIG. 4 is an illustrative process flow for implementing the system in accordance with some aspects of the invention.

As shown in FIG. 4, a process 100 is provided for monitoring inclination changes of the analyzer during operation, and triggering one or more actions (e.g., counter measures) if the inclination changes exceed one or more predetermined thresholds. At step 105, a determination is made as to whether the analyzer has been requested to start a test cycle for an analytical test. For example, the computing device using the measurement module is configured to make a determination as to whether an operator has inserted a cartridge into the port of the analyzer, and whether the analyzer has been prompted, e.g., via the I/O interface, to perform an analytical test using the cartridge. At step 110, acceleration data is collected during the test cycle. For example, the accelerometer may be configured to generate static acceleration data along up to three axes (x, y, z).

Figure 5:
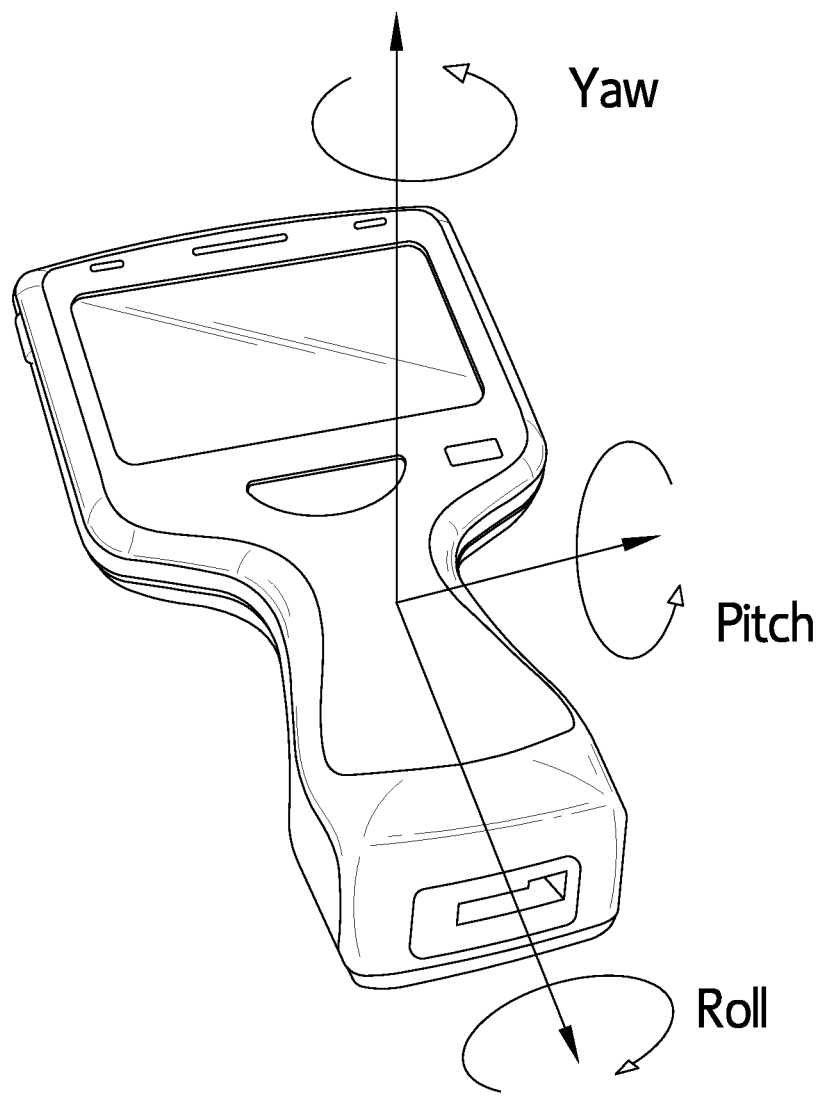
FIG. 5 shows roll, pitch, and yaw angles of an analyzer in accordance with some aspects of the invention.

At step 115, the acceleration data is used to determine the spatial orientation of the analyzer and the cartridge during the test cycle. For example, the computing device and/or the accelerometer may be configured to use the acceleration data along one or more of the three axes to calculate corresponding angular measurements for the one or more axes of the analyzer such that the spatial orientation of the analyzer may be determined with respect to roll, pitch, and yaw of the analyzer, as shown in FIG. 5.

As further shown in FIG. 4, at step 120, the determined spatial orientation of the analyzer is compared to a threshold operating spatial plane, e.g., ±20° of a horizontal plane of the base of the analyzer, more preferably ±15° of a horizontal plane, even more preferably ±10° of a horizontal plane. For example, the computing device may be configured to compare the spatial orientation of the analyzer to one or more predetermined threshold values stored in the memory (e.g., the values may be stored in a table or database). The predetermined threshold values may be independent of or dependent on the type of cartridge inserted into the analyzer. In additional embodiments of the present invention, the computing device may be configured to compare: (i) the roll of the analyzer to a predetermined threshold roll; (ii) the pitch of the analyzer to a predetermined threshold pitch; and (iii) the yaw of the analyzer to a predetermined threshold yaw, or, alternatively, a composite threshold of two or three values.

At step 125, if the spatial orientation of the analyzer exceeds the threshold operating spatial plane, one or more actions may be triggered. Specifically, if the computing device determines that the spatial orientation of the analyzer exceeds the threshold operating spatial plan, then the computing device may prompt the operator to take corrective action. For example, the computing device may send a notification alert to the display of the analyzer that instructs and/or illustrates corrective action including required movement of the analyzer with regard to the threshold operating spatial plane in order to prompt the operator into correcting the spatial orientation of the analyzer back within the threshold operating spatial plane during the test cycle.

Additionally or alternatively, the computing device may be configured to suppress a result of the analytical test if the computing device determines that the spatial orientation of the analyzer exceeds the threshold operating spatial plan. For example, the computing device may be configured to determine that the spatial orientation of the analyzer exceeded the threshold operating spatial plan for a predetermined amount of time and/or by a predetermined margin, and thus the integrity of the analytical test is compromised beyond correction and the test result should be suppressed. Furthermore, the computing device may also be configured to log the event of the calculated angular measurements exceeding the threshold values in a history log available for future use; interrupt or modify the test cycle in progress; lock the analyzer from completing or performing the analytical test, and/or correct the test result as discussed in further detail herein.

In the additional embodiments of the present invention, if the computing device determines that the determined roll of the analyzer exceeds the threshold roll, the determined pitch of the analyzer exceeds the threshold pitch, and/or the determined yaw of the analyzer exceeds the threshold yaw or composite threshold, then the computing device may trigger one or more actions, e.g., providing the alert prompting the user to take the corrective action during the test cycle, and/or suppressing the result of the analytical test.

At step 130, if the spatial orientation of the analyzer does not exceed the threshold operating spatial plane, the process continues monitoring starting at step 110 for the duration of the test cycle.

As with the previous embodiments described herein, one or more steps in the process described in connection with FIG. 4 may occur simultaneously or substantially simultaneously with other process steps and/or the order of the steps may be modified.

Detection of Improper Motion During Testing

In another embodiment, the invention pertains to a method and corresponding computing system and device configured to measure dynamic acceleration using the accelerometer and formulate a determination on whether one or more actions should be triggered based on the measured dynamic acceleration. In this aspect, the accelerometer is configured to measure the dynamic acceleration of the analyzer by itself or of both the analyzer and the cartridge, i.e., after the cartridge is inserted into the measurement module. Since some assays are sensitive to dynamic acceleration (e.g., immunometric testing), it is important to minimize the effects of motion for substantially the entire duration of a test cycle for these types of assays. Accordingly, in some aspects, the invention provides systems and processes for monitoring the motion of the analyzer during operation to ensure that the analyzer remains substantially motionless.

Figure 6:
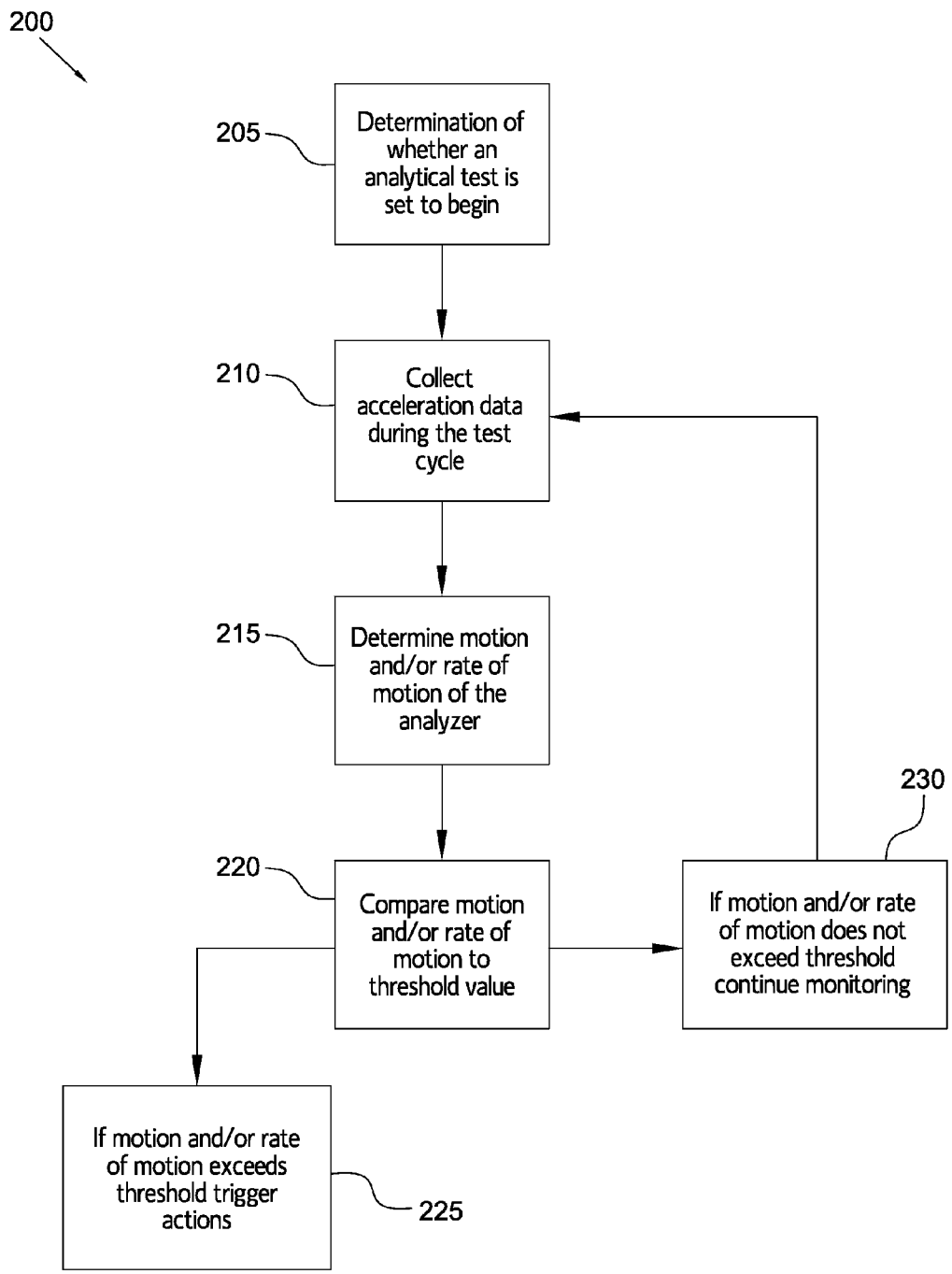
FIGS. 6-10 are illustrative process flows for implementing the system in accordance with some aspects of the invention.

As shown in FIG. 6, a process 200 is provided for monitoring the motion of the analyzer during operation and executing counter measures (trigger one or more actions) if the motion exceeds one or more predetermined thresholds. At step 205, a determination is made as to whether the analyzer has been requested to start a test cycle for an analytical test. For example, the computing device using the measurement module may be configured to make a determination as to whether an operator has inserted a cartridge into the port of the analyzer, and whether the analyzer has been prompted, e.g., via the I/O interface, to perform an analytical test using the cartridge. At step 210, acceleration data is collected during the test cycle. For example, the accelerometer may be configured to generate dynamic acceleration data.

At step 215, the acceleration data is used to determine whether there is any movement of the analyzer and/or the cartridge during the test cycle. For example, the computing device and/or the accelerometer may be configured to determine whether inertial forces are being applied to the analyzer through dynamic acceleration in one or more directions. Furthermore, the computing device and/or the accelerometer may be configured to calculate a rate of motion for the analyzer based on the acceleration data.

At step 220, the determined motion and/or rate of motion of the analyzer is compared to a predetermined threshold, e.g., a threshold rate of motion of about 50 meters/second$^2$, for the analyzer. For example, the computing device may be configured to compare the motion and/or rate of motion of the analyzer to one or more predetermined threshold values stored in the memory, e.g., the one or more predetermined thresholds may be stored in a table or database. The predetermined threshold value may be independent of or dependent on the type of cartridge inserted into the analyzer.

At step 225, if the motion and/or rate of motion of the analyzer exceeds the threshold rate of motion, one or more actions may be triggered. Specifically, if the computing device determines that the motion and/or rate of motion of the analyzer exceeds the threshold rate of motion, then the computing device may prompt the operator to take corrective action. For example, the computing device may send a notification alert to the display of the analyzer that instructs and/or illustrates corrective action including the cessation or deceleration of movement of the analyzer with regard to the threshold rate of motion in order to prompt the operator into correcting the motion of the analyzer below the threshold rate of motion.

Additionally or alternatively, the computing device may be configured to suppress a result of the analytical test if the computing device determines that the motion and/or rate of motion of the analyzer exceeds the threshold rate of motion. For example, the computing device may be configured to determine whether the motion and/or rate of motion of the analyzer exceeds the threshold rate of motion for a predetermined amount of time and/or by a predetermined margin, and thus whether the integrity of the analytical test has been compromised beyond correction, and whether the test result should be suppressed. Furthermore, the computing device may also be configured to log the event of the motion and/or rate of motion exceeding the threshold value in a history log available for future use; interrupt or modify the test cycle in progress; and/or correct the test result as discussed in further detail herein.

At step 230, if the motion and/or rate of motion of the analyzer does not exceed the threshold rate of motion, the process continues monitoring starting at step 210 for the duration of the test cycle.

As should be understood by one of skill, the processes 100 and 200 may be performed separate of one another or as a single process. The processes 100 and 200 may be performed sequentially or simultaneously. Further, the processes 100 and 200 may be performed independent of or dependent on the type of cartridge inserted into the analyzer. For example, in the instance that an immunometric cartridge is detected inserted within the port of the analyzer, the process 200 may be the only process executed, whereas in the instance that a hematocrit cartridge is detected inserted within the port of the analyzer, the process 100 may be the only process executed. Advantageously, this may save on computations by the processor and preserve battery life of the analyzer.

Detection of Improper Spatial Orientation and/or Motion During Specific Stages of the Test Cycle In another embodiment, the processes of the invention and related systems may further include a step of formulating determinations based on a stage of the test cycle. For example, during a test cycle, a typical cartridge may be performing a number of actions or steps to ultimately sense a target analyte within a sample. These steps may include among others (i) actuation steps in which fluid is being moved from one location of the cartridge to another; (ii) incubation steps in which reactions are being promoted to proceed; (iii) mixing steps in which different fluids and reagents are being combined; (iv) washing steps in which fluids are being rinsed from a particular location, e.g., the sensor region; and (v) detection steps in which analytes and/or signals are being read or detected. The threshold values used to determine whether one or more actions should be triggered may be stage specific and/or the triggered one or more actions may be stage specific. Accordingly, in some aspects, the invention relates to systems and processes for monitoring the spatial orientation and/or motion of the analyzer during one or more stages, optionally each stage, of the test cycle, and formulating determinations based on the stage of the test cycle in which one or more events occur.

Figure 7:
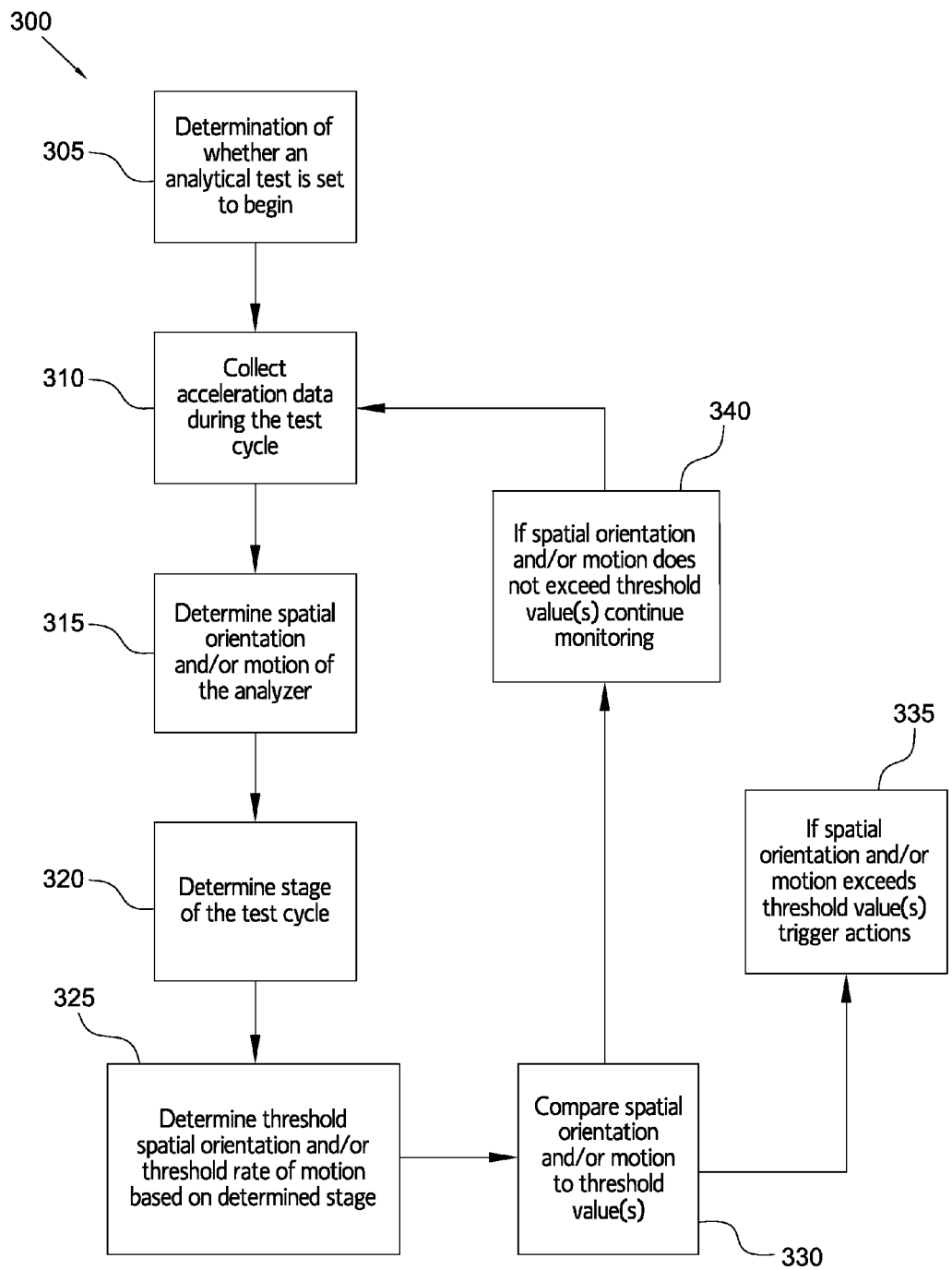

As shown in FIG. 7, the process 300 may start at step 305 where a determination is made as to whether the analyzer has been requested to start a test cycle for an analytical test, as described with respect to FIGS. 4 and 6. At step 310, acceleration data is collected during the test cycle. For example, the accelerometer may be configured to collect static and/or dynamic acceleration data. In additional embodiments of the present invention, the computing device and/or the accelerometer may be configured to determine the roll, pitch, and/or yaw of the analyzer, as discussed above with respect to FIG. 4.

At step 315, the acceleration data is used to determine the spatial orientation of the analyzer and/or whether there is any movement of the analyzer during the test cycle. At step 320, a stage of the test cycle is determined. For example, the computing device may be configured to determine at what stage of the test cycle (e.g., actuation stage, incubation stage, mixing stage, wash stage, or detection stage) the analyzer and cartridge are currently functioning. At step 325, a threshold operating spatial plane and/or threshold rate of motion are determined based on the determined stage of the test cycle. For example, the computing device may be configured to access a table or database and select the threshold operating spatial plane and/or the threshold rate of motion based on the determined stage of the test cycle. In additional embodiments of the present invention, the computing device may be configured to determine a predetermined threshold roll, a predetermined threshold pitch, and/or a predetermined threshold yaw based on the determined stage of the test cycle.

At step 330, the determined spatial orientation and/or motion and/or rate of motion of the analyzer is compared to the determined threshold(s) selected based on the current stage of the test cycle. In additional embodiments of the present invention, the computing device may be configured to compare the roll of the analyzer to the predetermined threshold roll, the pitch of the analyzer to the predetermined threshold pitch, and/or the yaw of the analyzer to the predetermined threshold yaw or composite threshold, based on the determined stage of the test cycle.

At step 335, if the spatial orientation and/or motion and/or rate of motion of the analyzer exceeds at least one of the determined threshold(s), one or more actions may be triggered. Specifically, if the computing device determines that the spatial orientation and/or motion and/or rate of motion of the analyzer exceeds at least one of the determined threshold(s), then the computing device may send a notification to the operator and/or prompt the operator to take corrective action. Furthermore, the computing device may also be configured to log the event in a history log available for future use; interrupt or modify the test cycle in progress; and/or correct the test result as discussed in further detail herein.

At step 340, if the spatial orientation and/or motion and/or rate of motion of the analyzer does not exceed determined threshold(s), the process continues monitoring starting at step 310 for the duration of the test cycle.

As with the previous embodiments described herein, one or more steps in the process described in connection with FIG. 7 may occur simultaneously or substantially simultaneously with other process steps and/or the order of the steps may be modified. For example, the step of determining the stage of the test cycle may occur before, concurrently with, or after the step of determining spatial orientation and/or motion of the analyzer.

Detection of Improper Spatial Orientation and/or Motion for Self-Correction

In another embodiment of the present invention, the processes described herein may further include correcting a signal from at least one sensor based on whether an improper spatial orientation and/or motion of the analyzer has been detected and optionally on the relative degree of the improper spatial orientation and/or motion of the analyzer. For example, the processes may include determining a correction factor associated with the spatial orientation and/or motion of the analyzer, e.g., from a look up table, correction algorithm, or the like, and applying the correction factor to a signal generated by the sensor to produce a corrected signal.

In alternative embodiments, the processes described herein may also include correcting or modifying at least one process of the test cycle, e.g., modifying a timing of the test cycle, based on whether improper spatial orientation and/or motion of the analyzer has been detected. For example, the process may include a step of determining improper spatial orientation and/or motion of the analyzer, and modifying an incubation stage of the test cycle such that a test analyte and a signal antibody are in contact with one another for a longer (or shorter) period of time. Accordingly, in some aspects, the invention relates to systems and processes for monitoring the spatial orientation and/or motion of the analyzer during the test cycle, and self-correcting an analyte signal or at least one process step of the test cycle, e.g., incubation period, if the spatial orientation and/or motion of the analyzer exceeds predetermined thresholds.

Figure 8:
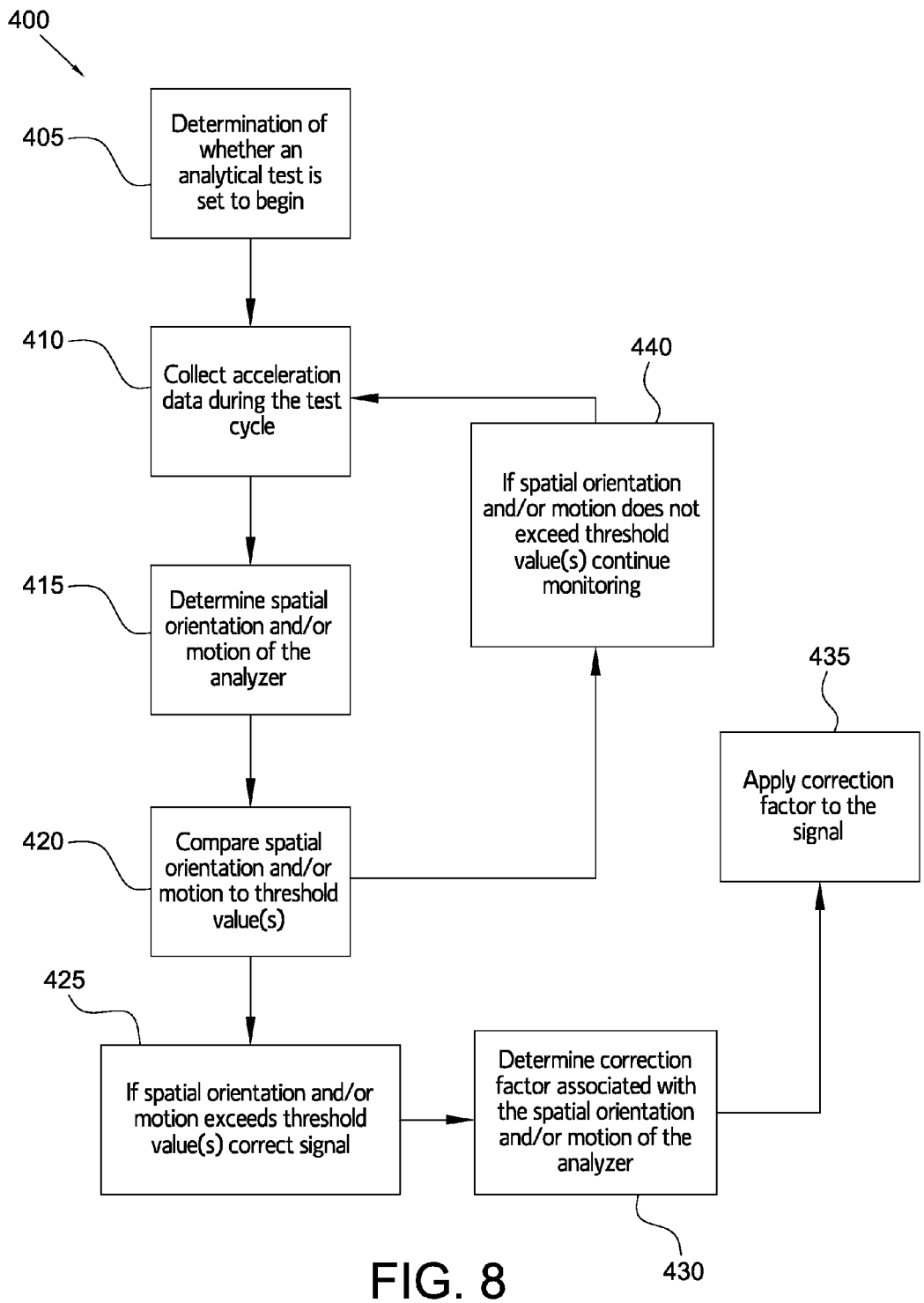

As shown in FIG. 8, the process 400 may start at step 405 where a determination is made as to whether the analyzer has been requested to start a test cycle for an analytical test, as described with respect to FIGS. 4 and 6. At step 410, acceleration data is collected during the test cycle. For example, the accelerometer may be configured to collect static and/or dynamic acceleration data. In additional embodiments of the present invention, the computing device and/or the accelerometer may be configured to determine the roll, pitch, and/or yaw of the analyzer, as discussed above with respect to FIG. 4.

At step 415, the acceleration data is used to determine the spatial orientation of the analyzer and/or whether there is any movement of the analyzer during the test cycle. At step 420, the determined spatial orientation and/or motion and/or rate of motion of the analyzer is compared to predetermined threshold(s). In the additional embodiments of the present invention, the computing device may be configured to compare the roll of the analyzer to a predetermined threshold roll, the pitch of the analyzer to a predetermined threshold pitch, and/or the yaw of the analyzer to a predetermined threshold yaw, or alternatively a composite threshold.

At step 425, if the spatial orientation and/or motion and/or rate of motion of the analyzer exceed the determined threshold(s), one or more actions may be triggered. Specifically, if the computing device determines that the spatial orientation and/or motion and/or rate of motion of the analyzer exceeds at least one of the determined threshold(s), then the computing device may at step 430 determine a correction factor associated with the spatial orientation and/or motion of the analyzer, e.g., from a look up table, correction algorithm, or the like, and, at step 435, apply the correction factor to a signal generated by the sensor to produce a corrected signal. The correction factor may include a blood non-homogeneity correction factor, a blood cell sedimentation correction factor, and/or a blood motion factor. A blood non-homogeneity factor may be determined experimentally by running a set of test devices at different pitch orientations, e.g. zero degrees, five degrees, ten degrees . . . ninety degrees (or some subset thereof), and recording the response of a given sensor, e.g., hematocit. This may be repeated for yaw and roll and also for a range of analyte concentrations, e.g., hematocrit concentrations, zero, 20%, 40% and 60%. In this way a family of curves relating "true analyte" at zero degrees versus "measured analyte" is obtained as a function of orientation. By embedding an algorithm derived from these data into the instrument, the instrument can then determine the correction factor to apply for any given measured orientation. Where the non-homogeneity relates to red blood cells, the correction factor addresses sedimentation. With respect to a blood motion factor, this is determined experimentally by running a set of test devices while applying different motions to the instrument (using robotics programmed to repeat a controlled motion) and recording the response of a given sensor, e.g. troponin. This is repeated over a range of analyte concentrations, and again a family of curves relating "true analyte" (zero motion) versus "measured analyte" is obtained as a function of various motions. By embedding an algorithm derived from these data into the instrument, the instrument can then determine a motion and find the nearest embedded model analog to that motion. A look-up table is then used to find a correction factor to apply for any given recorded motion.

In alternative embodiments, steps 430 and 435 may include correcting and/or modifying at least one process step of the test cycle. For example, the computing device may be configured to modify the timing of the test cycle upon the determination that the spatial orientation and/or motion and/or rate of motion of the analyzer exceeds at least one of the determined threshold(s).

At step 440, if the spatial orientation and/or motion and/or rate of motion of the analyzer do not exceed at least one of the predetermined threshold(s), the process continues monitoring starting at step 410 for the duration of the test cycle.

As with the previous embodiments described herein, one or more steps in the process described in connection with FIG. 8 may occur simultaneously or substantially simultaneously with other process steps and/or the order of the steps may be modified.

Operation and Verification of the Analyzer

As discussed in detail herein, acceleration data collected by the accelerometer can be used to determine the spatial orientation and motion of the analyzer during a testing cycle that can potentially compromise the integrity of an analytical test being performed by the analyzer. Some embodiments of the invention, however, are not limited to collecting acceleration data only during a testing cycle. For example, acceleration data may be collected by the accelerometer intermittently or continuously throughout the day, and optionally including during the testing cycle operation.

The detected spatial orientation and mechanical shock or vibration outside of the testing cycle operation may be used to determine an operational state of the analyzer, e.g., whether the analyzer is in use or in a state of rest, character recognized input for the analyzer, an operational status of the analyzer, e.g., whether the analyzer is performing a function properly, and/or the analyzer is damaged. Specifically, the computing device may be configured to analyze the acceleration data generated by the accelerometer and compare the acceleration data levels with predetermined thresholds stored in the memory. A fall onto a hard surface, for example, can be detected by identifying free fall followed by very high deceleration generated by the impact. For example, the ADXL345 accelerometer features a built-in free fall detection. The computing device can monitor the sequence of events (e.g., a free fall followed by a high rate of deceleration) and trigger one or more actions. These actions may include; (i) logging the event in a history log available for future use (e.g., during repair of malfunctioning analyzers); (ii) displaying a warning or service indicator message for the operator; (iii) locking the analyzer until Quality Control is completed successfully (per procedures at user sites); (iv) performing internal diagnostics; (v) communicating, optionally via internet, the status of the analyzer to a central command service portal with the ability to place an automated request for a replacement unit if fault is detected, and/or; (vi) interrupting or modifying the test cycle in progress. Other similar functions will be apparent to those skilled in the art of point of care blood testing. For example, during product shipment, if the battery is connected to the analyzer, a log of shocks and vibration due to transportation can be generated. Upon delivery of the analyzer, the data corresponding to the shipping period can be examined to determine if shipping damage has occurred.

Power Management

In one embodiment, the analyzer may be a battery-powered handheld device for use in point-of-care analyte testing. The analyzer should be ready for use quickly and reliably. Therefore, power management of the analyzer is an important consideration to achieve maximum uptime and reliability. In particular, the analyzer can be placed in various states that achieve different levels of power savings, e.g., standby, sleep, and power off, based on the acceleration data received from the accelerometer.

Furthermore, depending on the power saving mode, wake-up times may be different. Unless the analyzer is always ON, the operator has to wait for the duration of the wake up to start testing operations. Therefore, the acceleration data can also be used to reduce the wait time. Accordingly, some aspects of the present invention provide a system and process for determining when to place the analyzer in different levels of power saving and when to wake up the analyzer for anticipated operation.

Figure 9:
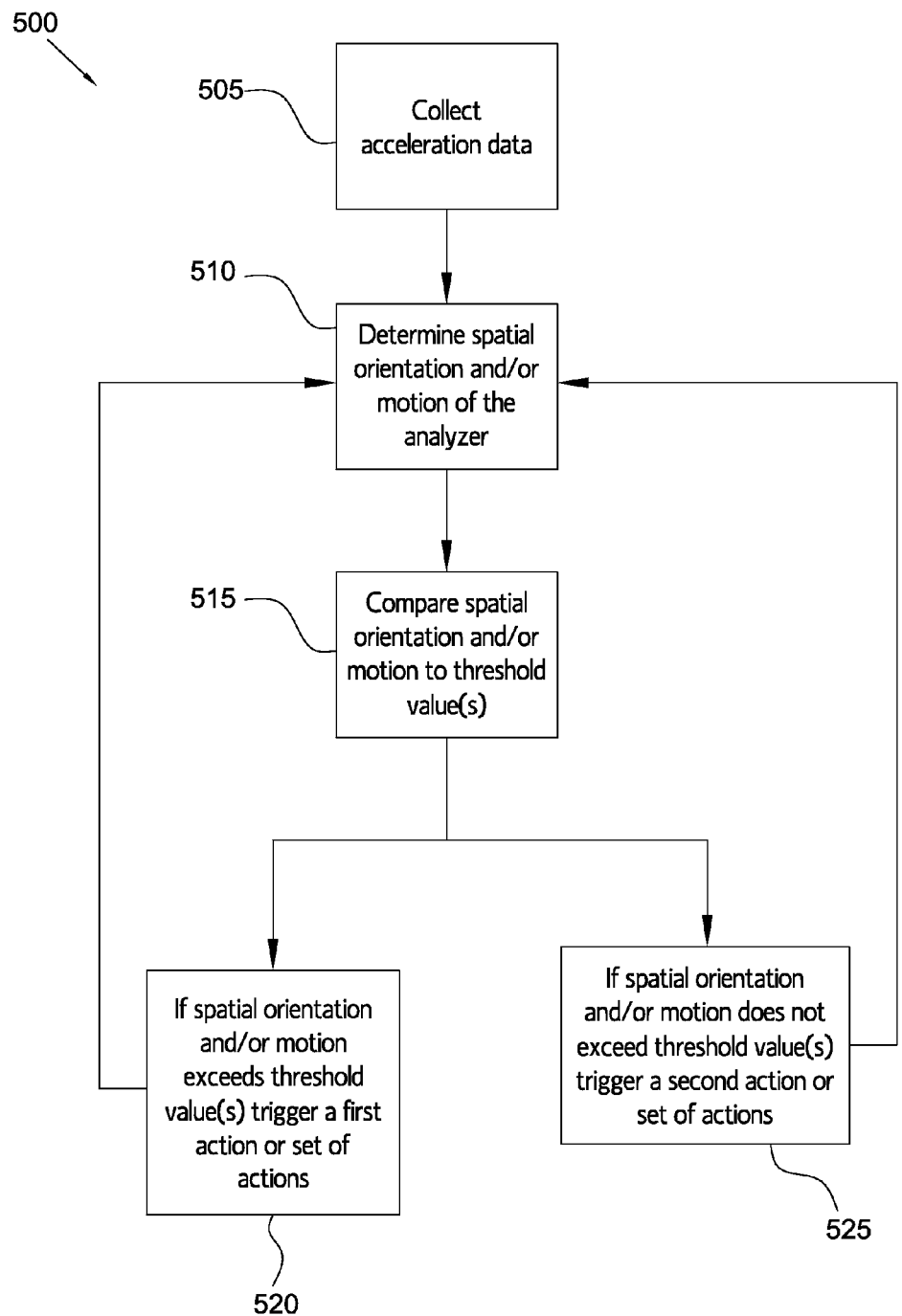

As shown in FIG. 9, the process 500 may start at step 505 where acceleration data is collected. For example, the accelerometer may be configured to collect static and/or dynamic acceleration data intermittently or continuously throughout the day. At step 510, the acceleration data is used to determine the spatial orientation of the analyzer and/or whether there is any movement of the analyzer. At step 515, the determined spatial orientation and/or motion and/or rate of motion of the analyzer is compared to predetermined threshold(s). For example, the spatial orientation and/or motion and/or rate of motion of the analyzer are compared to predetermined threshold(s) stored in the memory to determine whether the analyzer is in motion or not.

At step 520, if the spatial orientation and/or motion and/or rate of motion of the analyzer exceed at least one of the determined threshold(s), one or more actions (e.g., a first action or first set of actions) may be triggered. For example, if the computing device determines that the spatial orientation and/or motion and/or rate of motion of the analyzer exceed at least one of the determined threshold(s), then the computing device may determine that the analyzer is being moved and/or transported and initiate a power ON cycle concurrently or soon thereafter (e.g., once the analyzer is picked up by the operator) such that the analyzer is available for a subsequent anticipated operation.

At step 525, if the spatial orientation and/or motion and/or rate of motion of the analyzer do not exceed at least one of the determined threshold(s), one or more actions (e.g., a second action or second set of actions) may be triggered. For example, if the spatial orientation and/or motion and/or rate of motion of the analyzer do not exceed at least one of the predetermined threshold(s), then the computing device may determine that the analyzer has been left unattended in a resting position for a preset (or configurable) period of time and initiate a pre-set power saving mode(s) dependent on or independent of the period of time the analyzer has been left in the undisturbed position.

Detection of Proper Insertion of Cartridge

In one embodiment, the analyzer comprises electromechanical features for docking and locking a cartridge within the port, as discussed above with respect to FIGS. 1A-1C. Specifically, a cartridge latch within the analyzer may engage a feature located at a bottom of the cartridge and a spring action pushes the cartridge all the way into the port when cartridge is inserted into the port of the measurement module. Advantageously, these electromechanical features have several benefits including ensuring that the cartridge is engaged in the proper position, preventing the cartridge from moving during the test cycle, and providing tactile feedback to the operator indicating that the cartridge is properly inserted within the analyzer.

Furthermore, the measurement module may also be equipped with an electromechanical contact switch triggered by the cartridge when the cartridge is inserted in the correct position in the port. The computing device monitors the switch status and initiates the cartridge test cycle when the switch is activated. Similarly, the computing device may be configured to detect removal of the cartridge. However, the electromechanical features described above may require additional parts (e.g., follower arm, electromechanical switch, cables, and connectors) and additional features on the measurement module mechanical housing to guide the follower arm and position the switch. These parts and features may be potentially eliminated by using acceleration data.

For example, engagement of a cartridge latch when the cartridge is fully inserted in the analyzer creates a signature vibration profile that can be detected by the accelerometer(s). The computing device may be configured to compare the vibration profile for an inserted cartridge to a pre-established vibration profile stored in the memory to determine whether proper or full engagement of the cartridge has occurred. Accordingly, aspects of the present invention provide a system and processes for determining whether the cartridge is inserted properly into the analyzer using vibration profiles.

Figure 10:
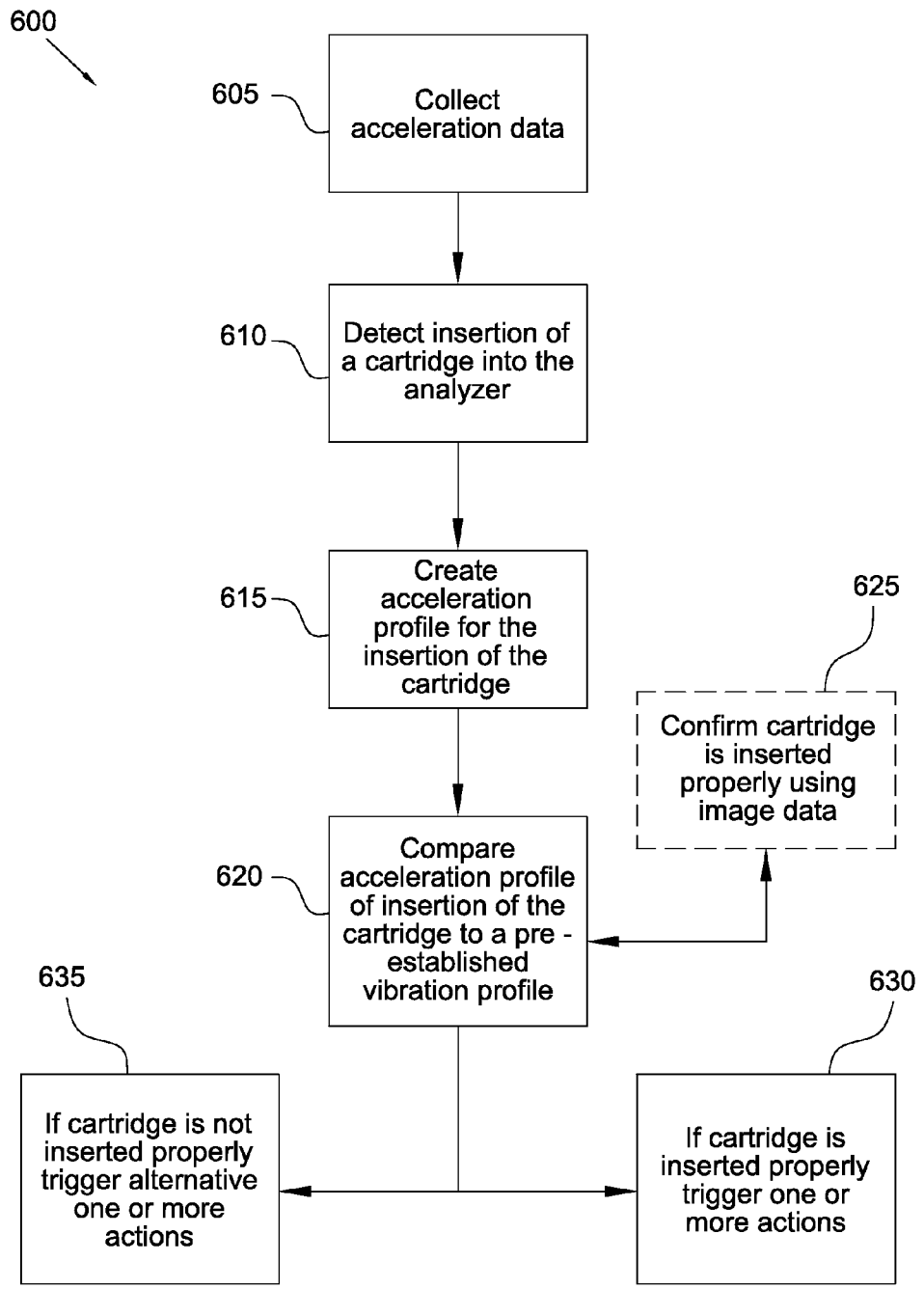

As shown in FIG. 10, the process 600 may start at step 605 where acceleration data is collected. For example, the accelerometer may be configured to collect static and/or dynamic acceleration data intermittently or continuously throughout the day. At step 610, the insertion of a cartridge into the port is detected. For example, an operator may engage a cartridge within the port of the measurement module such that an analytical test can be performed on a sample within the cartridge. The computing device may be configured to detect the insertion, e.g., sensing the engagement of the cartridge latch. At step 615, the acceleration data is used to create an acceleration profile for the insertion of the cartridge. For example, the computing device may be configured to use the acceleration data collected during the insertion of cartridge, which comprises vibrations characteristic of the electromechanical interaction between the cartridge and the analyzer during the insertion, to create a current vibration profile 650 (see, e.g., FIG. 11) for the insertion of the cartridge.

Figure 11:
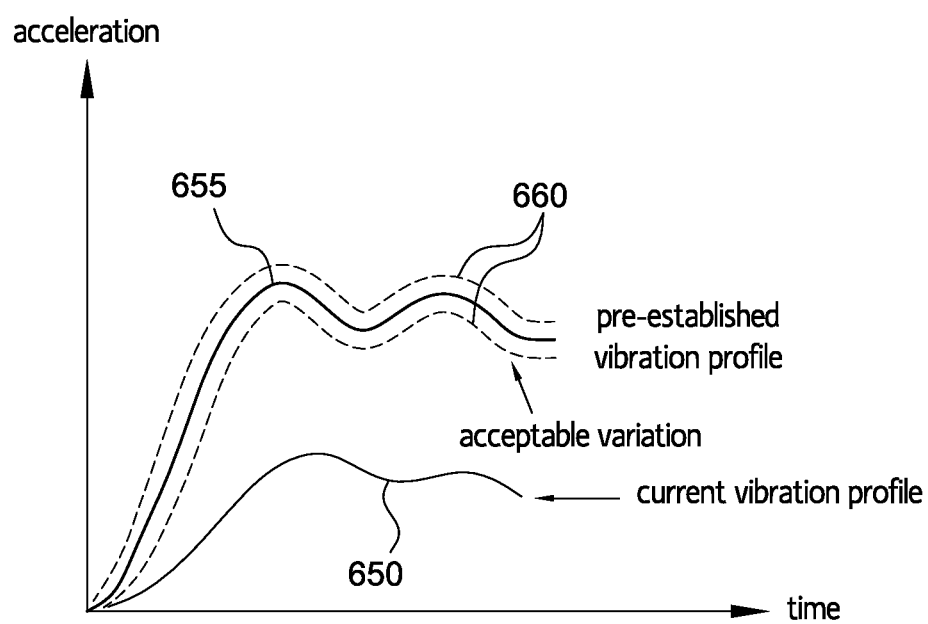
FIG. 11 shows vibration profiles of an analyzer in accordance with some aspects of the invention.

At step 620, the current vibration profile 650 for the insertion of the cartridge may be compared to a pre-established vibration profile 655 (e.g., a vibration profile pre-recorded for a proper insertion of a cartridge with the same analyzer). For example, as shown in FIG. 11, the computing device may be configured to compare the current vibration profile 650 to the pre-established vibration profile 655 and a band of expected variation 660 (e.g., a predetermined range of acceptable variation) stored in the memory to determine whether the cartridge is inserted properly or fully into the analyzer.

Optionally at step 625, an internal barcode reader (e.g., the imaging camera as discussed with respect to FIGS. 1A-1C) located in the measurement module of the analyzer can image the cartridge to confirm that the cartridge is correctly positioned in the port (see, e.g., U.S. Provisional Patent Application No. 61/579,816, which is incorporated herein by reference in its entirety). The image acquired by the barcode reader can be compared by the computing device with a reference image. Registration of the acquired image with the reference image previously stored in memory allows confirming that test cartridges are in the proper position. Optionally, features (e.g., 1-D or 2-D barcode, geometric feature, etc.) dedicated for positioning can be printed or embossed on a surface of the cartridge, e.g., the cartridge underside.

At step 630, if the cartridge is inserted properly or fully into the analyzer, one or more actions may be triggered. For example, if the computing device determines that the cartridge is inserted properly or fully into the analyzer, then the same computing device may initiate a test cycle for the cartridge. At step 635, if the cartridge is not inserted properly or fully into the analyzer, one or more alternative actions may be performed. For example, if the cartridge is not inserted properly or fully into the analyzer, then the computing device may send a notification to the operator and/or prevent initiation of the test cycle for the cartridge.

In a similar aspect, vibration profiles for one or more other process steps, e.g., pneumatic pumping, may be obtained and compared with a pre-established vibration profile, e.g., pre-established pneumatic pumping profile, and a band of expected variation (e.g., a predetermined range of acceptable variation) stored in the memory to determine whether the cartridge is being operated properly, e.g., whether the sample and/or wash or calibration fluid is being properly pumped during operation. In this example, if an improper pumping operation is detected, a user notification may be triggered and/or other corrective measures may be undertaken by the device to take into account the improper pneumatic pumping profile.

Data Entry Using Acceleration Data

In one embodiment, the analyzer comprises an I/O interface for data entry, as discussed above with respect to FIGS. 1A-1C. Specifically, a resistive touch-screen overlaid on the display and the external barcode scanner can be used for data entry, as shown in FIGS. 1A-1C. The barcode scanner is used to scan user and patient IDs, cartridge lots and types, control fluid lots, etc. During the interactive phase of the workflow, the operator responds to prompts displayed on the screen and selects the desired options by touching the screen directly. In addition to these two main methods, the accelerometers may also be used by the operator to enter data or trigger functions (e.g., a sequence of actions).

For example, the accelerometer may be configured to detect dynamic and static acceleration of the analyzer in space. During a learning session, the computing device may be configured to record the dynamic and static acceleration of the analyzer, e.g., motion characteristics associated with waving or shaking the analyzer. The motion sequences or characteristics of the analyzer associated with the recorded dynamic and static acceleration are then saved in the memory for future use as a reference. Thereafter, the operator may reproduce the specific motion sequences or characteristics in a normal operating mode of the analyzer. The computing device may detect the specific motion sequences or characteristics and compare the specific motion sequences or characteristics with reference sets of motion sequences or characteristics that are stored in the memory. Recognition of the motion sequences or characteristics by the computing device may trigger one or more actions. For example, a specific predetermined sequence of motions such as a quick shaking of the instrument can be used to trigger actions such as "scroll to next page" or "initiate a power ON cycle."

In another example, the accelerometer can be used to detect a vibration signature associated with gentle tapping, or tapping sequences, on the analyzer casing. During a learning session, the computing device may be configured to record the static and dynamic acceleration of the analyzer, e.g., vibration characteristics associated with tapping on the analyzer. The vibration characteristics are then stored in the memory for future use as a reference. Thereafter, the operator may reproduce the specific tapping sequence in a normal operating mode of the analyzer. The computing device may detect and compare the operator tapping with reference sets of tapping that are stored in the memory. Recognition of the motion or tapping sequences by the computing device may trigger a series of actions, including authorize operator access to the system, system activation or deactivation (e.g., placing the analyzer in OFF, sleeping or standby states), initiation of data download, initiation of a pre-set customizable series of actions, and initiation of network connection or connection with other devices. Optionally, the analyzer display screen may also be used to perform some of these functions. If the display screen is used, sliding gestures may be also used. Accordingly, aspects of the present invention provide a system and processes for data entry into the analyzer using the accelerometers.

Figure 12:
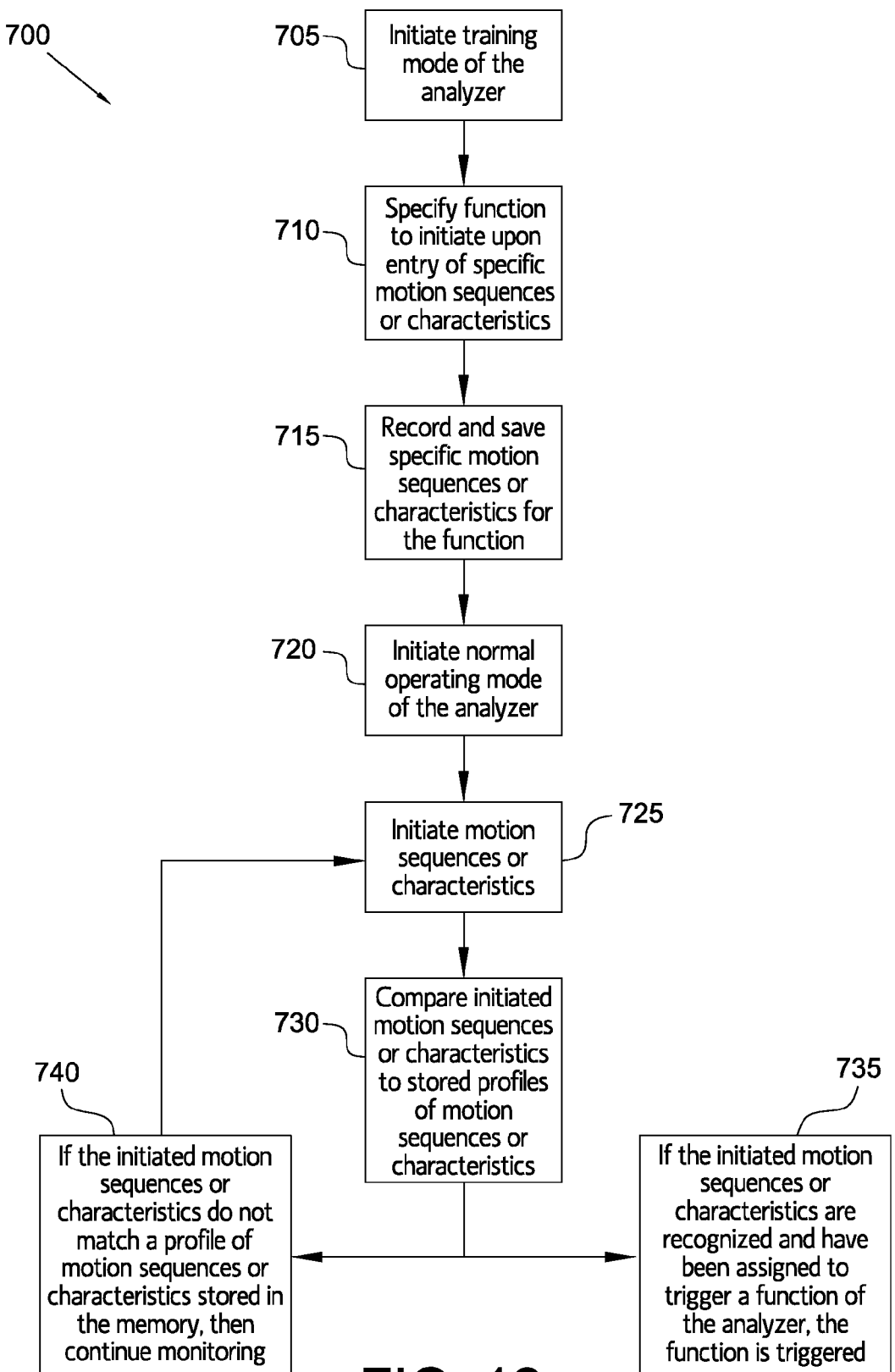
FIGS. 12-14 are illustrative process flows for implementing the system in accordance with some aspects of the invention.

As shown in FIG. 12, the process 700 may start at step 705 where an operator triggers a training mode of the analyzer. For example, the operator may use the I/O interface to trigger a training mode of the analyzer whereby an interactive learning session may be initiated for teaching the analyzer motion sequences or characteristics. At step 710, the operator may specify a specific function to be initiated upon entry of specific motion sequences or characteristics. For example, the analyzer may be configured to trigger actions such as "scroll to next page" or "initiate a power ON cycle" upon receiving specific motion sequences or characteristics. At step 715, the specific motion sequences or characteristics may be recorded by the analyzer and saved in the memory. For example, the computing device may be configured to collect static and/or dynamic acceleration data during a recording session and save the acceleration data as a specific profile of motion sequences or characteristics.

At step 720, the operator may trigger a normal operating mode of the analyzer. At step 725, motion sequences or characteristics may be initiated by an operator, and the initiated motion sequences and characteristics may be detected by the accelerometer and/or computing device. For example, the operator may repeat substantially the same motion sequences or characteristics previously recorded in step 715, and the repeated motion sequences and characteristics may be detected by the accelerometer and/or computing device. At step 730, the initiated motion sequences or characteristics may be compared to a stored archive of profiles of motion sequences or characteristics. For example, the computing device may be configured to compare the initiated motion sequences or characteristics to the profiles of motion sequences or characteristics stored in the memory to determine whether the initiated motion sequences or characteristics have been assigned to trigger a function of the analyzer. At step 735, if the initiated motion sequences or characteristics are recognized and have been assigned to trigger a function of the analyzer, the function may be triggered. For example, if the initiated motion sequences or characteristics match the profile of motion sequences or characteristics stored in the memory, then the computing device may execute or initiate the function assigned to the profile of motion sequences or characteristics stored in the memory.

At step 740, if the initiated motion sequences or characteristics do not match a profile of motion sequences or characteristics stored in the memory, the process continues monitoring starting at step 725.

Initiating a Predetermined Sequence of Events Using Acceleration Data

In one embodiment, a state of the analyzer may be inferred by the acceleration data and used to trigger a predetermine sequence of events. For example, typically an external simulator may be inserted into the port of the analyzer at specific time intervals, e.g., once a week. The external simulator helps determine if calibration of thermistors of the analyzer has drifted such that the thermistors are out of specification. This may be performed by thermally shorting the thermistors and comparing their outputs. If their outputs match, then the thermistors are synchronized. However, the functionality of the external simulator may be replaced by sampling the accelerometer data to identify a long period of time where the analyzer has been undisturbed. This implies that the two thermistors would be at thermal equilibrium.

In another example, the acceleration data can be used to identify long stretches of time when the analyzer is typically not disturbed, such as between midnight and 3 am, e.g., a time convenient for the user. The computing device may be configured to perform housekeeping activities (such as downloading software updates) during such time. Accordingly, some aspects of the present invention provide systems and processes for initiating a predetermined sequence of events using the acceleration data.

Figure 13:
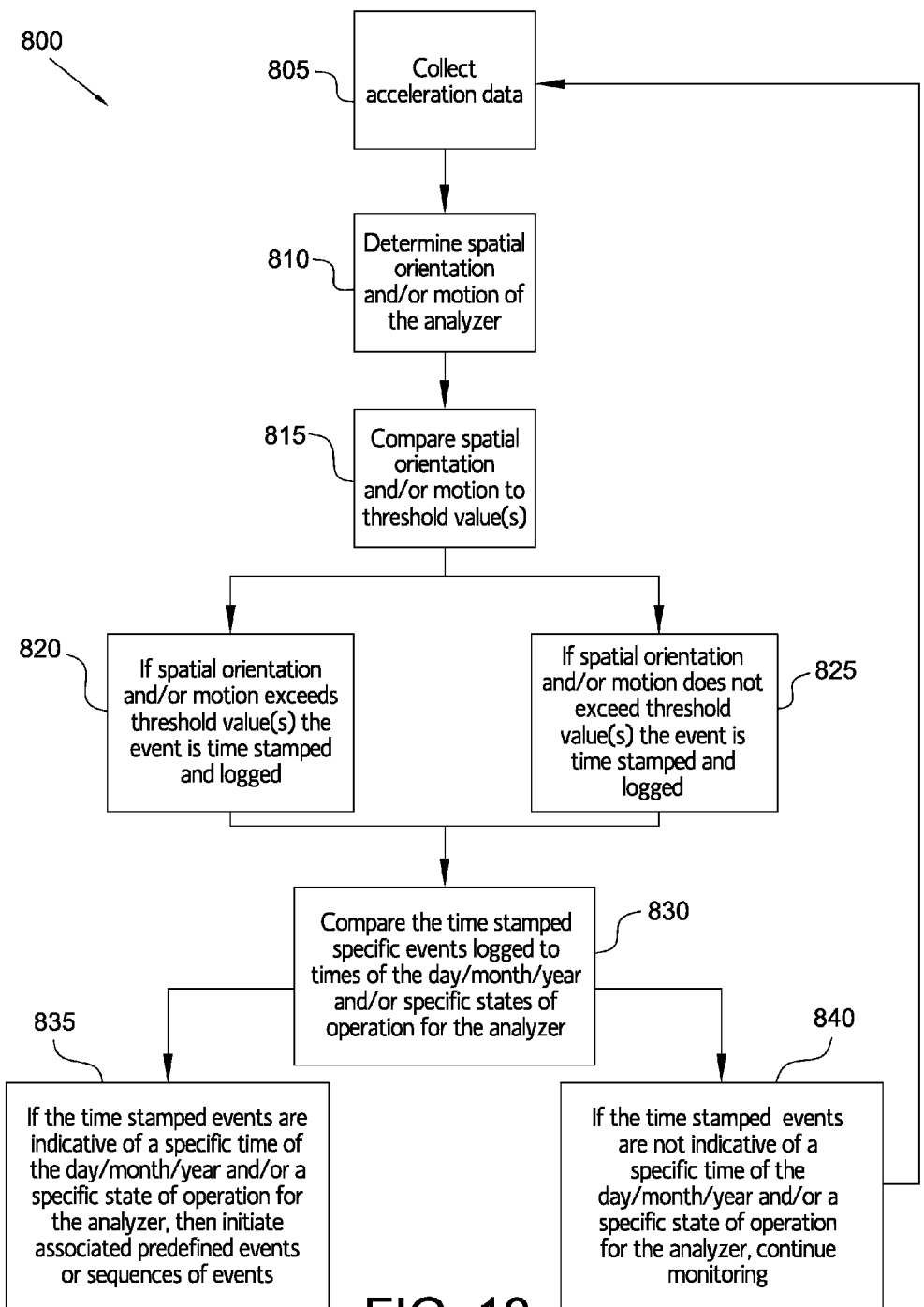

As shown in FIG. 13, the process 800 may start at step 805 where acceleration data is collected. For example, the accelerometer may be configured to collect static and/or dynamic acceleration data intermittently or continuously throughout the day. At step 810, the acceleration data is used to determine the spatial orientation of the analyzer and/or whether there is any movement of the analyzer. At step 815, the determined spatial orientation and/or motion and/or rate of motion of the analyzer is compared to predetermined threshold(s). For example, the spatial orientation and/or motion and/or rate of motion of the analyzer are compared to predetermined threshold(s) stored in the memory to determine whether the analyzer is in motion or not.

At step 820, if the spatial orientation and/or motion and/or rate of motion of the analyzer exceed the predetermined threshold(s), the event is time stamped and logged in a table or database within the memory. For example, if the computing device determines that the spatial orientation and/or motion and/or rate of motion of the analyzer exceed the predetermined threshold(s), then the computing device may determine that the analyzer is being moved and/or trans-ported, and time stamp and log the event in a table or database such that the data is available for subsequent determinations.

At step 825, if the spatial orientation and/or motion and/or rate of motion of the analyzer do not exceed the predetermined threshold(s), the event is time stamped and logged in a table or database within the memory. For example, if the computing device determines that the spatial orientation and/or motion and/or rate of motion of the analyzer does not exceed the predetermined threshold(s), then the computing device may determine that the analyzer is stationary, and time stamp and log the event in a table or database such that the data is available for subsequent determinations.

At step 830, the time stamped events logged in the table and database are compared to a table or database including specific times of the day/month/year and/or specific states of operation for the analyzer during which associated predefined events or sequences of events may take place. At step 835, if the time stamped events logged in the table and database are indicative of a specific time of the day/month/year and/or a specific state of operation for the analyzer, then the computing device may initiate the associated predefined events or sequences of events. For example, the computing device may be configured to identify a long period of time where the analyzer has been undisturbed (a state of operation) and initiate a recording in the memory that the thermistors are at thermal equilibrium and/or identify a long stretch of time when the analyzer is typically not disturbed, confirm that the analyzer has been undisturbed for a predetermined amount of time (a state of operation), and download software updates.

At step 840, if the time stamped events logged in the table and database are not indicative of specific times of the day/month/year and/or a specific state of operation for the analyzer, the process continues monitoring starting at step 805.

Detection of Free Fall

In one embodiment, the analyzer comprises free fall detection capabilities such that the detection of free fall may be used to trigger one or more actions by the computing device. For example, the ADXL345 accelerometer features built-in free fall detection. FDA publication of 30 Jan. 2008 entitled "Recommendations Clinical Laboratory Improvement Amendments of 1988 (CLIA) waiver applications for Manufacturers of In Vitro Diagnostics Devices" recommends including lock-out functions that do not allow output of results if the device was mishandled (e.g. dropped) and the device detects damage during internal electronic system checks. Many institutional users of point-of-care devices require that performance verification tests should be performed if an analyzer is dropped. Without means of automated free fall detection, meeting this requirement is dependent on self-reporting of the event by the operator. However, a point-of-care instrument equipped with an accelerometer may be configured to make the determination, reporting, and performance of the verification itself.

Furthermore, the computing device may also be configured such that the analyzer performs impact reducing actions upon the detection of a free fall. For example, the computing device may be configured to retract actuators in the measurement module and/or turn off the power to the display to reduce the effect of the impact on the analyzer. Accordingly, some aspects of the present invention provide systems and processes for detecting free fall of the analyzer and triggering one or more actions if the analyzer is currently in free fall or has experienced a free fall event.

Figure 14:
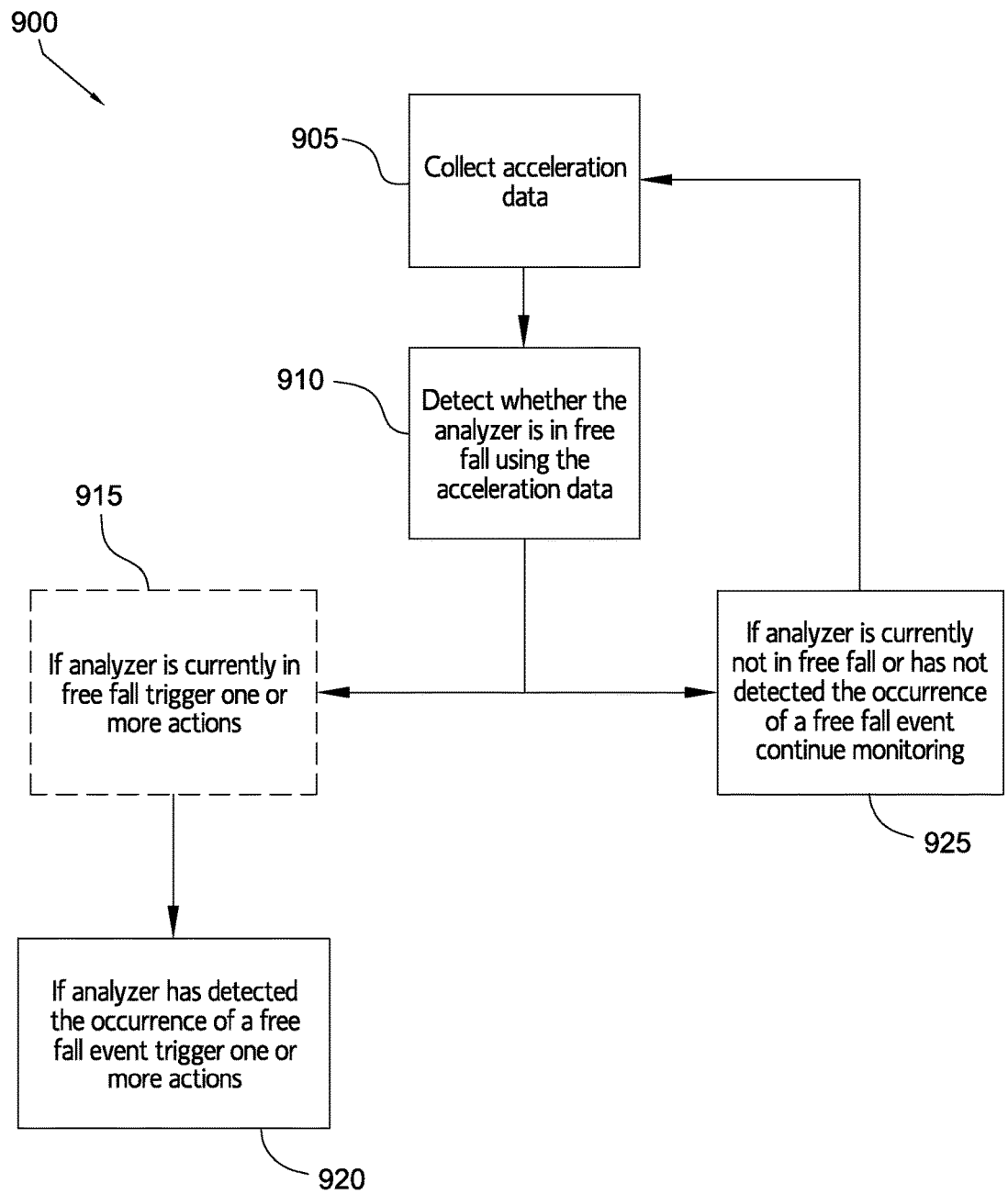
Figure 15:
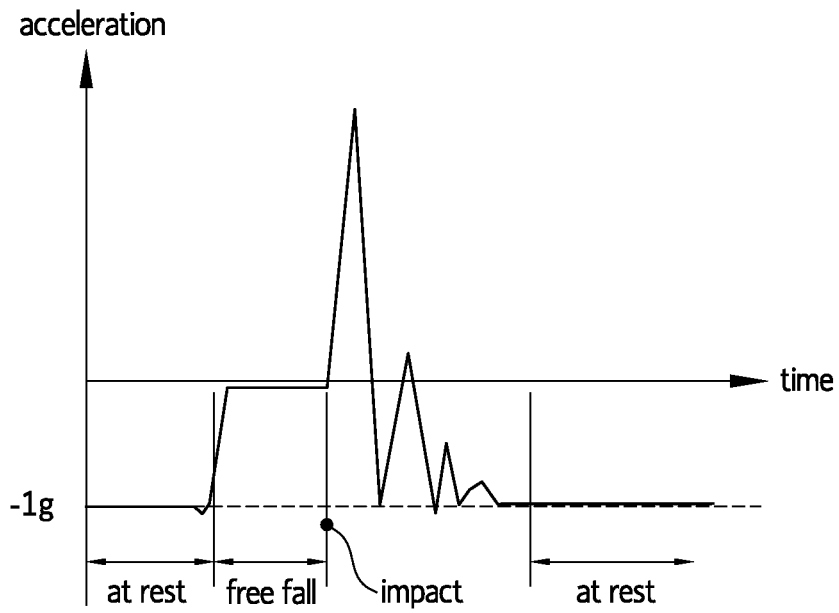
FIGS. 15 and 16 show acceleration profiles of an analyzer in accordance with some aspects of the invention.
Figure 16:
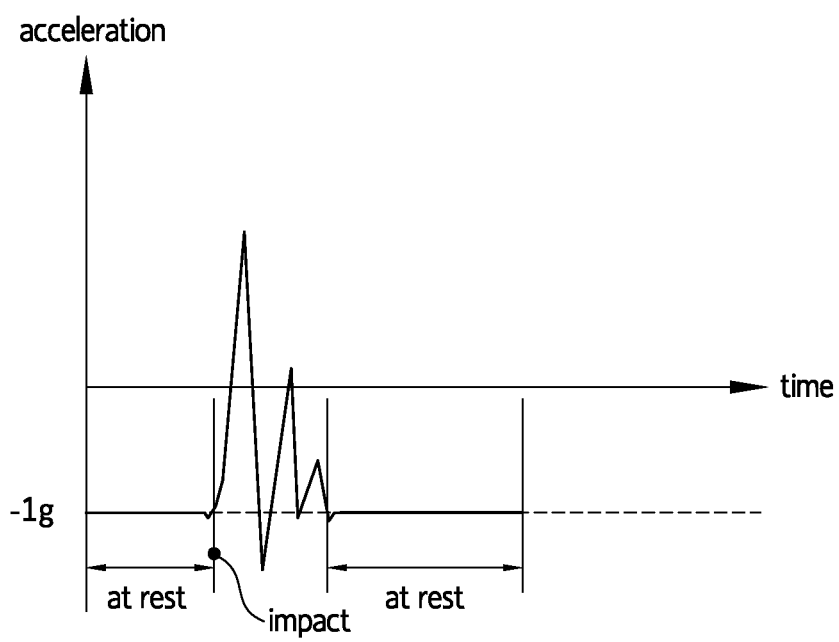

As shown in FIG. 14, the process 900 may start at step 905 where acceleration data is collected. For example, the accelerometer may be configured to collect static and/or dynamic acceleration data intermittently or continuously throughout the day. At step 910, the acceleration data is used to detect whether the analyzer is in free fall or has undergone free fall followed by a subsequent impact. For example, the computing device may be configured to use the acceleration data collected to determine whether the accelerometer senses free fall as a predetermined value (e.g., zero or $g_o$) and a sudden change in acceleration caused by the subsequent impact. The accelerometer reads only the gravitational acceleration when the instrument is at rest. If the instrument is dropped from a surface of a table or while being carried by a user, the accelerometer senses the free fall as a predetermined value (e.g., zero or close to zero within prespecified limits). A sudden change in acceleration is observed when the analyzer impacts the floor. Thus, the free fall and subsequent impact create a plateau and spike profile on a graph of the acceleration data over time that can be interpreted by the computing device as the detection of a free fall occurrence (as shown in FIG. 15). A different profile of acceleration is observed if the analyzer undergoes accidental impact, such as the operator inadvertently hitting the analyzer on the corner of a table while carrying the analyzer (as shown in FIG. 16).

Optionally at step 915, if the analyzer is detected as currently being in a state of free fall, the computing may be configured to perform one or more actions to reduce the effect of the impact on the analyzer and reduce the risk of injury to the operator. For example, upon the detection that the analyzer is currently in free fall, the computing device may be configured to retract actuators in the measurement module and/or turn off the power to the display.

At step 920, if the analyzer is detected as having been in a state of free fall and suffered a subsequent impact, the computing may be configured to perform one or more actions. For example, upon the detection that the analyzer has experienced a free fall event, the computing device may be configured to lock the analyzer from operation, send an alert or notification the operator (e.g., provides a notification on the display or sends a notification to the operator or a designator person via wireless connectivity), perform a system diagnostics, time-stamp when the analyzer is locked, perform a system verification in accordance with regulatory requirements, time-stamp when the system verification is performed, store the time-stamps in an electronic auditable system, determine whether the system performance verification fails, and/or communicate the failure of the system performance verification to the electronic auditable system.

In additional embodiments, the electronic auditable system may be configured to perform replacement of the analyzer, and the computing device may be configured to display a status of the replacement on the analyzer. Further, the computing device may be configured to communicate automatically and wirelessly an operational status of the analyzer to a remote entity, e.g., a predetermined person at a hospital. The alert may include a visual alarm, an audible alarm, a notice on a display screen of the analyzer, and a message sent wirelessly to a predetermined entity, e.g., a person responsible for integrity of the system, a distributor of the system, and/or a manufacturer of the system.

At step 925, if the acceleration data is not indicative of the occurrence of a free fall event, the process continues monitoring starting at step 905.

Detection of Properly Functioning Analyzer

Figure 17:
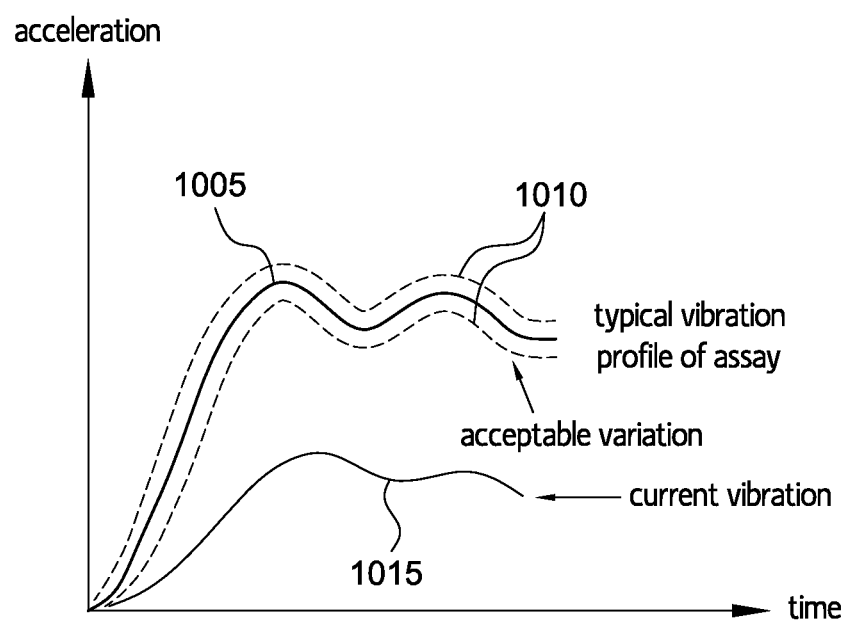
FIG. 17 shows vibration profiles of an analyzer in accordance with some aspects of the invention.

In one embodiment, the analyzer comprises electromechanical features for performing a test cycle on the cartridge, as discussed above with respect to FIGS. 1A-1C. Specifically, the measurement module that interfaces with the cartridge moves multiple plungers in predetermined trajectories when the analyzer runs a specific cartridge (assay). This actuation creates a vibration profile 1005 for a typical cartridge (as shown in FIG. 17). Around the vibration profile of the typical cartridge, there is a band of expected variation 1010 that represents manufacturing variation (of the cartridge and/or analyzer), environmental variation, etc. After a cartridge is run, the vibration profile of that cartridge 1015 can be compared with the typical profile 1005 for a similar cartridge. Deviations from the typical profile 1005 may be used to indicate conditions that could require preventive maintenance. For example, a deviation from the typical profile 1005 could indicate parts about to get loose in the analyzer that would eventually require preventive maintenance. Accordingly, some aspects of the present invention provide systems and processes for detecting whether the analyzer is functioning properly using vibration profiles.

Furthermore, the measurement module may also be equipped with an electromechanical contact switch triggered by the cartridge when the cartridge is inserted in the correct position in the port. The computing device monitors the switch status and initiates the cartridge test cycle when the switch is activated. Similarly, the computing device may be configured to detect removal of the cartridge. However, the electromechanical features described above require additional parts (e.g., follower arm, electromechanical switch, cables, and connectors) and additional features on the measurement module mechanical housing to guide the follower arm and position the switch. These parts and features may be potentially eliminated by using acceleration data.

For example, engagement of a cartridge latch when the cartridge is fully inserted in the analyzer creates a signature vibration profile that can be detected by the accelerometer(s). The computing device may be configured to compare the vibration profile for an inserted cartridge to a pre-established vibration profile stored in the memory to determine whether proper or full engagement of the cartridge has occurred. Accordingly, aspects of the present invention provide a system and processes for determining whether the analyzer is functioning properly using vibration profiles.

Figure 18:
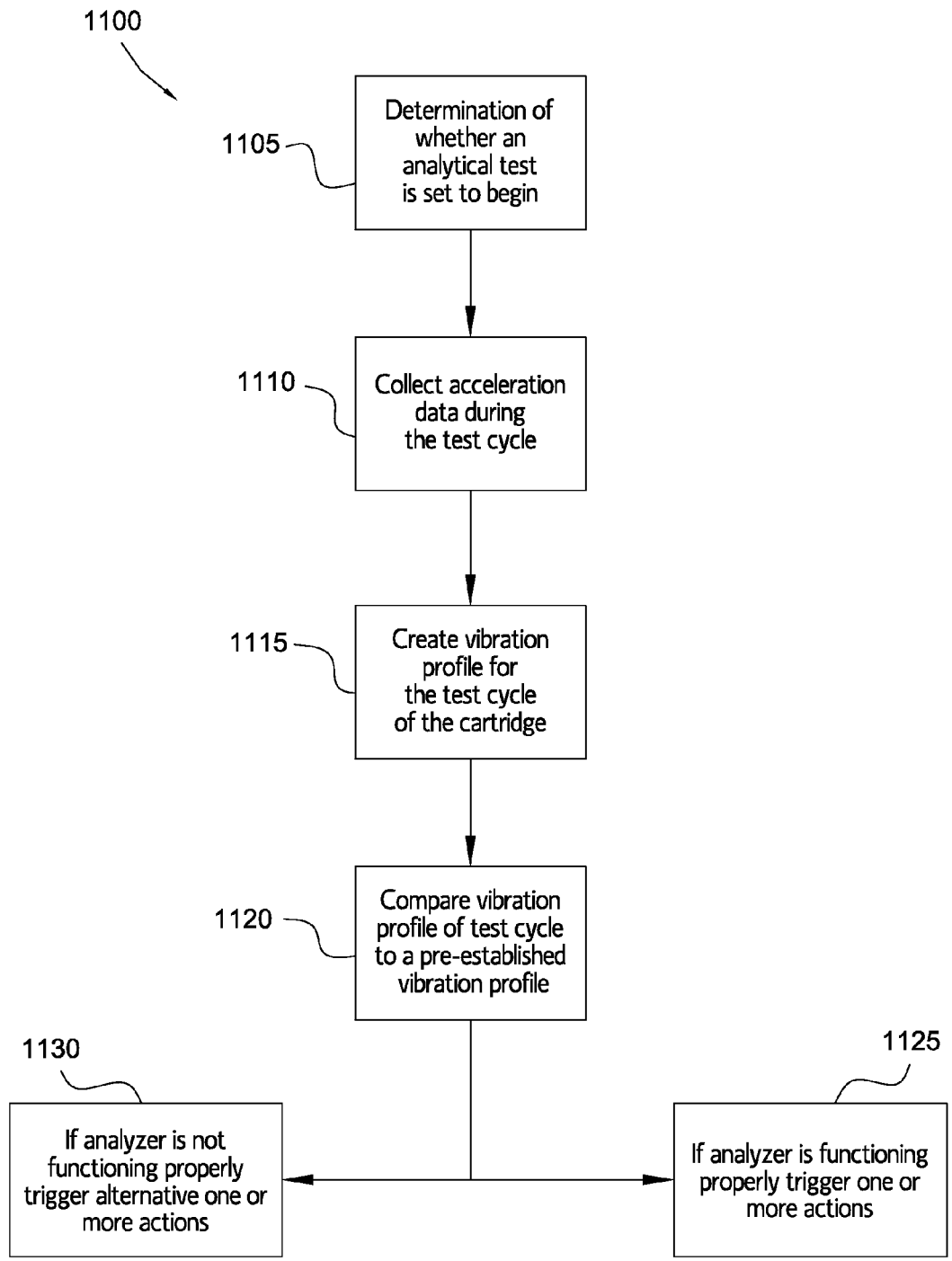
FIG. 18 is an illustrative process flow for implementing the system in accordance with some aspects of the invention.

As shown in FIG. 18, the process 1100 may start at step 1105 where a determination is made as to whether the analyzer has been requested to start a test cycle for an analytical test. At step 1110, acceleration data is collected during the test cycle. For example, the accelerometer may be configured to collect static and/or dynamic acceleration data. At step 1115, the acceleration data is used to create an acceleration profile for the test cycle of the cartridge. For example, the computing device may be configured to use the acceleration data collected during the test cycle of the cartridge, which comprises vibrations characteristic of the electromechanical interaction between the cartridge and the analyzer during the test cycle, to create a vibration profile for the test cycle of the cartridge.

At step 1120, the vibration profile for the test cycle of the cartridge may be compared to a pre-established vibration profile, e.g., a vibration profile pre-recorded for a proper test cycle of a similar cartridge with the same analyzer. For example, as shown in FIG. 17, the computing device may be configured to compare the vibration profile 1015 to the pre-established vibration profile 1005 and the band of expected variation 1010 (e.g., a predetermined range of acceptable variation) to determine whether the analyzer is functioning properly.

At step 1125, if the analyzer is functioning properly, one or more actions may be triggered. For example, if the computing device determines that the analyzer is functioning properly, then the computing device may log the event or send a notification to the operator. At step 1130, if the analyzer is not functioning properly, one or more alternative actions may be performed. For example, if the analyzer is not functioning properly, then the computing device may send a notification to the operator, perform system maintenance, and/or prevent reporting of the test result.

Combining Data Input Received from a Multitude of Sensors to Achieve Various Objectives In additional or alternative embodiments, the analyzer comprises on-board sensors additional to that of the accelerometers 25 for performing a test cycle on the cartridge, as discussed above with respect to FIGS. 1A-1C. Specifically, the program code of the analyzer 10 may collect data acquired at any time from one or more on-board sensors, e.g., a temperature sensor, an ambient light sensor, a barometric pressure sensor, an imaging camera, etc. The collected data may be used by the analyzer 10 alone or in combination with the acceleration and/or inertial data collected by the accelerometers for various functions of the analyzer. For example, the measurement of the temperature and barometric pressure during the test cycle may also be used as correction factors for the generation of assay results. The temperature sensors may also be used to measure the ambient temperature at the time of testing, and the collected ambient temperature data may also be used by the analyzer to prevent the delivery of results if the measured ambient temperature is outside of an operational range. Measurement of the ambient light may be used to automatically adjust the illumination intensity of the analyzer display. Moreover, the imaging camera may be configured to read the barcodes on the cartridges.

The data collected by the on-board sensors and the acceleration and/or inertial data collected from the accelerometers may have additional uses if communicated to a central device, e.g., a central computer server, where the collected data from the on-board sensors and accelerometers may be further analyzed and processed into actionable information. The actionable information may then be used by customers and/or additional entities such as R&D personnel, Technical Support services, and Marketing in support of the IVD instrument system. For example, the actionable information may be used to obtain a better characterization of the environments where the analyzers are used as a source of information for the investigation of customer issues, and for design inputs relevant to design enhancements or future designs of the IVD instrument system. Examples of the data that may be useful include: (i) ambient temperature extremes and averages, (ii) average barometric pressure and extremes, and (iii) lighting environments, including determination of artificial and natural light. This data may be used individually, or in combination with other sources of information, such as the acceleration and/or inertial information (collected from the accelerometers) and cartridge consumption information (as described in jointly owned U.S. Pat. No. 7,263,501, which is incorporated herein by reference in its entirety), to determine usage patterns for customer facilities.

Advantageously, various aspects of the invention described herein provide for systems and processes capable of (a) detection of mechanical abuse or potentially abusive vibration, shock or motion imposed on the analyzer, (b) enhanced power management and potential extension of battery life on a single charge, (c) elimination or reduction of some electromechanical features, (d) enhancement of user interface, and (e) elimination or detection of artifacts due to uncontrolled motion of the biological sample fluid in a test cartridge during the testing cycle by using an internal motion sensor (accelerometer or other) to detect disadvantageous motion or angle changes from an ideal position.

For purposes of illustration and not limitation, the following examples provide information on the effect of inclination changes, cell sedimentation, and non-homogeneity of cells in a hematocrit assay.

EXAMPLE 1

The present example characterizes the effect that analyzer orientation may have on a hematocrit assay measurement especially for blood samples with a low hematocrit and a high sedimentation rate.

Patient blood samples from a variety of units in a hospital were collected. Upon the arrival of each sample to the lab, approximately 1 ml of blood was drawn from the sample tube and placed in a plain tube for use in the present example. Relevant sample identification information including sample code and unit code were recorded. The sample was mixed with a roller mixer for at least five minutes and then tested with four analyzers, two of which were positioned at level (0°) and two positioned at a 45° pitch angle. The cartridges used for the study were CHEM6+ (which measures glucose, urea, sodium, potassium, chloride and hematocrit) and CHEM8+ (which measures glucose, creatinine, urea, total carbon dioxide, sodium, potassium, calcium, chloride and hematocrit.

If the hematocrit values from the two tilted analyzers were different from those of the two level analyzers by 2% packed cell volume (PCV) or more, further testing was performed on the sample. Hematocrit measurements under a variety of analyzer pitch angles (0°, ±30°, ±45°, ±60°), spun hematocrit, and an improvised "Micro" erythrocyte sedimentation rate (ESR) were further investigated.

Among 169 samples, 18 showed some different results between level (0°) and 45°, and the samples were tested further under various analyzer pitch angles (0°, ±30°, ±45°, ±60°). For each pitch angle, the average hematocrit of each pair of analyzers was calculated. The highest and the lowest hematocrit values and the related pitch angles were extracted. The difference between the highest hematocrit value and the lowest hematocrit value of each sample is included in Table 1 below. A regression between hematocrit value and pitch angle was performed for each of the 18 samples and the regression slope is listed in Table 1 as well.

The maximum difference between the highest and the lowest hematocrit was 7.2% PCV observed from Sample No 4. The highest hematocrit occurred at −45° (analyzer head down) and the lowest hematocrit occurred at +60° (analyzer head up). All the samples in Table 1 showed the same trend, that is, the highest value was observed at a head down position and the lowest observed at a head up position, which is also demonstrated by the negative regression slopes. Accordingly, the following conclusions were drawn from the data obtained: hematocrit measured with the analyzer may be affected by analyzer pitch angles during blood measurement for patient blood samples with low hematocrit value and high sedimentation rate. The hematocrit value may read lower with the analyzer tilted up and read higher with the analyzer tilted down.

TABLE 1

| Sample No. | Highest Hct. Value (% PCV) | Pitch Angle (°) | Lowest Hct. Value (% PCV) | Pitch Angle (°) | Hct. Difference (% PCV) | Regression Slope (% PCV/°) |
|---|---|---|---|---|---|---|
| 4 | 23.2 | −45 | 16.0 | 60 | 7.2 | −0.0621 |
| 32 | 25.0 | −45 | 19.5 | 45 | 5.5 | −0.0409 |
| 49 | 23.2 | −60 | 19.5 | 60 | 3.7 | −0.0276 |
| 51 | 20.5 | −30 | 17.9 | 45 | 2.6 | −0.0178 |
| 58 | 25.8 | 0 | 23.3 | 60 | 2.5 | −0.0157 |
| 60 | 25.3 | −30 | 20.6 | 60 | 4.7 | −0.0282 |
| 65 | 25.7 | −60 | 23.3 | 60 | 2.4 | −0.0207 |
| 92 | 32.8 | 0 | 30.3 | 45 | 2.5 | −0.0560 |
| 97 | 22.6 | −60 | 20.7 | 60 | 1.9 | −0.0164 |
| 101 | 28.2 | −60 | 25.8 | 45 | 2.4 | −0.0157 |
| 102 | 23.4 | −45 | 20.3 | 45 | 3.1 | −0.0216 |
| 115 | 26.1 | −45 | 20.6 | 60 | 5.5 | −0.0356 |
| 116 | 28.7 | −30 | 25.6 | 45 | 3.1 | −0.0225 |
| 123 | 30.9 | −45 | 27.9 | 45 | 3.0 | −0.0163 |
| 129 | 28.2 | −45 | 26.1 | 45 | 2.1 | −0.0152 |
| 135 | 27.0 | −45 | 24.9 | 60 | 2.1 | −0.0135 |
| 154 | 26.5 | −45 | 24.3 | 60 | 2.2 | −0.0198 |
| 164 | 25.9 | −60 | 21.8 | 45 | 4.1 | −0.0298 |

EXAMPLE 2

The present example characterizes the effect pitch angle and/or roll angle may have on a hematocrit assay measurement especially for blood samples with a low hematocrit and a high sedimentation rate.

Patient blood samples were collected. Each sample was centrifuged at 5000 rpm for 5 minutes to separate plasma and blood cells. The plasma and blood cells were then reconstituted to obtain a sample of 18% PCV and ±2% PCV. The sample was then tested with analyzers at a vertical pitch between +45° and −45°. If the sample exhibited significant orientation effect, as described above with respect to Example 1, then the sample was set aside for further testing. The further testing included testing the sample with analyzers at a 0° and ±20° pitch angle (−20° referring to a head-down tilt and +20° referring to a head-up tilt), 0° and ±20° roll angle (−20° referring to a left angle tilt and +20° referring to a right angle tilt), and a compound angles (pitch & roll). The cartridges used for the study were E3+ (which tests sodium, potassium and hematocrit) and CHEM8+.

In a total of five donors that were tested, two did not show significant differences between +45° and −45° analyzer angles, and thus these samples were discarded. The remaining three samples were used to complete the study, and the relevant data is summarized below in Table 2. Among all test events (various angles of pitch and roll) only one sample (Sample 3 at a pitch angle of −20° and a roll angle of 0° (Event 11)) demonstrated a hematocrit bias value greater than allowed error. However, this anomaly may have been the result of a spurious experimental error unrelated to analyzer angle. All other results were within allowed error. Accordingly, the following conclusions were drawn from the data obtained: the analyzer orientation effect on hematocrit results is unlikely to give rise to clinically significant errors when the analyzer is maintained to within ±20° of level.

TABLE 2

| Event No. | Pitch Angle | Roll Angle | Mean Hematocrit of each event | | | Bias of each event | | |
|---|---|---|---|---|---|---|---|---|
| | | | Sample 1 | Sample 2 | Sample 3 | Sample 1 | Sample 2 | Sample 3 |
| 1 | 45 | 0 | 14.8 | 15.0 | 17.4 | | | |
| 2 | −45 | 0 | 16.7 | 19.4 | 22.0 | | | |
| 3 | 20 | −20 | 15.8 | 17.7 | 17.0 | −0.6 | 0.2 | −1.4 |
| 4 | 0 | 10 | 16.8 | 18.0 | 18.4 | 0.4 | 0.5 | −0.1 |
| 5 | 0 | −20 | 16.3 | 16.8 | 17.8 | −0.1 | −0.7 | −0.6 |
| 6 | −20 | 20 | 16.9 | 18.4 | 18.9 | 0.5 | 0.9 | 0.5 |
| 7 | 0 | −10 | 17.2 | 17.1 | 18.4 | 0.9 | −0.4 | −0.1 |
| 8 | −20 | −20 | 16.3 | 17.3 | 18.3 | −0.1 | −0.2 | −0.1 |
| 9 | 0 | 20 | 15.7 | 17.6 | 18.6 | −0.7 | 0.1 | 0.2 |
| 10 | 20 | 0 | 16.1 | 17.2 | 17.0 | −0.3 | −0.3 | −1.4 |
| 11 | −20 | 0 | 16.9 | 17.7 | 21.9 | 0.5 | 0.2 | 3.5 |
| 12 | 0 | 0 | 16.5 | — | 18.5 | 0.1 | — | 0.0 |
| 13 | 20 | 20 | 16.9 | 17.2 | 18.0 | −0.5 | −0.3 | −0.5 |
| 14 | −10 | 0 | 16.5 | 17.2 | 18.6 | 0.1 | −0.3 | 0.2 |
| 15 | 10 | 0 | 16.0 | 17.6 | 18.3 | −0.3 | 0.1 | −0.1 |
| 16 | −45 | 0 | 17.6 | 18.3 | 23.1 | | | |
| 17 | 45 | 0 | 15.7 | 16.1 | 13.2 | | | |

While the invention has been described in terms of various preferred embodiments, those skilled in the art will recognize that various modifications, substitutions, omissions and changes can be made without departing from the spirit of the present invention. It is intended that the scope of the present invention be limited solely by the scope of the following claims. In addition, it should be appreciated by those skilled in the art that a plurality of the various embodiments of the invention, as described above, may be coupled with one another and incorporated into a single reader device.

We claim:

1. A portable clinical system for performing an immunoassay on a biological sample, the system comprising:
    a test device comprising a sample entry port and a sensing region comprising an immunosensor for performing the immunoassay on the biological sample, which generates an electric signal based on a concentration of an analyte in the biological sample determined by the immunoassay; and
    an analyzer to initiate a test cycle of the test device, including performance of the immunoassay, comprising:
        a processor, a computer readable memory, and a non-transitory computer readable storage medium;
        a port to receive the test device;
        an accelerometer to collect data during the test cycle;
        program instructions stored on the non-transitory computer readable storage medium for execution by the processor via the computer readable memory, the program instructions comprising:
            program instructions to determine motion of the analyzer during a test cycle of the test device based on the data collected by the accelerometer during the test cycle;
            program instructions to compare the determined motion to a threshold rate of motion for the test device; and
            program instructions to at least one of: (i) provide an alert prompting a user to take corrective action during the test cycle, (ii) correct a result of the immunoassay, and/or (iii) suppress the result of the immunoassay, when the determined motion exceeds the threshold rate of motion.

2. The system of claim 1, wherein the analyzer further comprises program instructions to provide the alert prompting the user to take the corrective action during the test cycle, when the determined motion exceeds the threshold rate of motion.

3. The system of claim 1, wherein the analyzer further comprises program instructions to suppress the result of the immunoassay, when the determined motion exceeds the threshold rate of motion.

4. The system of claim 1, wherein the analyzer further comprises program instructions to correct the result of the immunoassay, when the determined motion exceeds the threshold rate of motion.

5. The system of claim 1, wherein the analyzer further comprises program instructions to provide the alert prompting the user to take the corrective action during the test cycle, and suppress the result of the immunoassay, when the determined motion exceeds the threshold rate of motion.

6. The system of claim 1, the analyzer further comprises program instructions to provide the alert prompting the user to take the corrective action during the test cycle, and correct the result of the immunoassay, when the determined motion exceeds the threshold rate of motion.

7. The system of claim 1, wherein the threshold rate of motion is no more than about 50 meters/second.

8. The system of claim 1, wherein the analyzer further comprises program instructions to measure dynamic acceleration based on the data collected by the accelerometer during the test cycle to determine the motion of the analyzer.

9. The system of claim 1, wherein the analyzer further comprises:
program instructions to determine spatial orientation of the analyzer during the test cycle of the test device based on the data collected by the accelerometer during the test cycle;
program instructions to compare the determined spatial orientation to a threshold operating spatial plane for the test device; and
program instructions to at least one of: (i) provide a different alert prompting the user to take different corrective action during the test cycle, (ii) correct the result of the immunoassay, and/or (iii) suppress the result of the immunoassay, when the determined spatial orientation exceeds the threshold operating spatial plane.

10. The system of claim 9, wherein the providing the different alert prompting the user to take the different corrective action comprises displaying the different alert on the analyzer and the different alert instructs the user to move the spatial orientation of the analyzer below the threshold operating spatial plane.

11. The system of claim 9, wherein:
the providing the different alert prompting the user to take the different corrective action comprises displaying the different alert on the analyzer and the different alert instructs the user to move the spatial orientation of the analyzer below the threshold operating spatial plane; and
the analyzer further comprises:
program instructions to detect a change in the spatial orientation of the analyzer during the test cycle;
program instructions to determine a new spatial orientation of the analyzer;
program instructions to compare the determined new spatial orientation to the threshold operating spatial plane; and
program instructions to complete the test cycle and provide the result of the immunoassay when the determined new spatial orientation is below the threshold operating spatial plane.

12. The system of claim 9, wherein:
the analyzer further comprises a base having a horizontal plane; and
the threshold operating spatial plane is no more than about 15° from the horizontal plane of the base.

13. The system of claim 12, wherein the threshold operating spatial plane is no more than about 10° from the horizontal plane of the base.

14. The system of claim 9, wherein:
the analyzer further comprises a base having a horizontal plane;
the port is substantially aligned to a first plane parallel to the horizontal plane of the base; and
the immunosensor is substantially aligned to a second plane parallel to the horizontal plane of the base.

15. The system of claim 14, wherein the threshold operating spatial plane is no more than about 15° from the horizontal plane of the base.

16. The system of claim 15, wherein:
the providing the different alert prompting the user to take the different corrective action comprises displaying the different alert on the analyzer and the different alert instructs the user to move the spatial orientation of the analyzer below the threshold operating spatial plane; and
the analyzer further comprises:
program instructions to detect a change in the spatial orientation of the analyzer during the test cycle based on the data collected by the accelerometer during the test cycle;
program instructions to determine a new spatial orientation of the analyzer;
program instructions to compare the determined new spatial orientation to the threshold operating spatial plane; and
program instructions to complete the test cycle and provide the result of the immunoassay when the determined new spatial orientation is below the threshold operating spatial plane.

17. The system of claim 9, wherein the analyzer further comprises program instructions to measure static acceleration on at least three axes of the analyzer based on the data collected by the accelerometer during the test cycle to determine the spatial orientation of the analyzer, and the determining the spatial orientation comprises determining at least one of roll, pitch, and yaw of the analyzer based on the measured static acceleration on the at least three axes of the analyzer.

18. The system of claim 17, wherein:
the comparing the determined spatial orientation to the threshold operating spatial plane comprises at least one of:
comparing the determined roll of the analyzer to a threshold roll;
comparing the determined pitch of the analyzer to a threshold pitch; and
comparing the determined yaw of the analyzer to a threshold yaw; and
the at least one of: (i) the providing the different alert prompting the user to take the different corrective action during the test cycle, (ii) the correcting the result of the immunoassay, and/or (iii) the suppressing the result of the immunoassay, when the determined spatial orientation exceeds the threshold operating spatial plane comprises at least one of: (i) providing the different alert prompting the user to take the different corrective action during the test cycle, (ii) correcting the result of the immunoassay, and/or (iii) suppressing the result of the immunoassay, when at least one of: (i) the determined roll of the analyzer exceeds the threshold roll, (ii) the determined pitch of the analyzer exceeds the threshold pitch, and/or (iii) the determined yaw of the analyzer exceeds the threshold yaw.

19. The system of claim 1, wherein:

the analyzer further comprises program instructions to determine a stage of the test cycle and program instructions to determine the threshold rate of motion based on the determined stage of the test cycle;

the comparing the determined motion to the threshold rate of motion comprises comparing the determined motion to the determined threshold rate of motion for the determined stage of the test cycle; and the at least one of: (i) the providing the different alert prompting the user to take the different corrective action during the test cycle, (ii) the correcting the result of the immunoassay, and/or (iii) the suppressing the result of the immunoassay, when the determined motion exceeds the threshold rate of motion comprises at least one of: (i) providing the different alert prompting the user to take the different corrective action during the test cycle, (ii) correcting the result of the immunoassay, and/or (iii) suppressing the result of the immunoassay, when the determined motion exceeds the determined threshold rate of motion for the determined stage of the test cycle.

* * * * *